United States Patent
Kotanko et al.

(10) Patent No.: US 12,040,092 B2
(45) Date of Patent: Jul. 16, 2024

(54) REAL-TIME INTRADIALYTIC HYPOTENSION PREDICTION

(71) Applicant: FRESENIUS MEDICAL CARE HOLDINGS, INC., Waltham, MA (US)

(72) Inventors: Peter Kotanko, New York, NY (US); Hanjie Zhang, Rutherford, NJ (US)

(73) Assignee: FRESENIUS MEDICAL CARE HOLDINGS, INC., Waltham, MA (US)

(*) Notice: Subject to any disclaimer, the term of this patent is extended or adjusted under 35 U.S.C. 154(b) by 313 days.

(21) Appl. No.: 16/897,430

(22) Filed: Jun. 10, 2020

(65) Prior Publication Data

US 2021/0193317 A1   Jun. 24, 2021

Related U.S. Application Data

(60) Provisional application No. 62/951,259, filed on Dec. 20, 2019.

(51) Int. Cl.
| | |
|---|---|
| G16H 50/20 | (2018.01) |
| A61M 1/14 | (2006.01) |
| G06N 5/04 | (2023.01) |
| G06N 20/00 | (2019.01) |
| G16H 10/60 | (2018.01) |

(Continued)

(52) U.S. Cl.
CPC .............. *G16H 50/20* (2018.01); *A61M 1/14* (2013.01); *G06N 5/04* (2013.01); *G06N 20/00* (2019.01); *G16H 10/60* (2018.01); *G16H 20/40* (2018.01); *G16H 50/30* (2018.01); *A61M 2230/30* (2013.01)

(58) Field of Classification Search
CPC ........ G16H 50/20; G16H 20/40; G16H 10/60; G16H 50/30; G06N 20/00; G06F 18/2413; Y10S 128/924; Y10S 706/924
See application file for complete search history.

(56) References Cited

U.S. PATENT DOCUMENTS

| | | | |
|---|---|---|---|
| 11,627,918 B2 * | 4/2023 | Nakamura | A61B 5/4094 600/500 |
| 2009/0163776 A1 * | 6/2009 | Inbar | G16H 50/70 600/301 |

(Continued)

FOREIGN PATENT DOCUMENTS

| | | | |
|---|---|---|---|
| JP | 2018043003 A | 3/2018 | |
| JP | 2019213858 A | 12/2019 | |

(Continued)

OTHER PUBLICATIONS

Lin, Cheng-Jui, "Intelligent system to predict intradialytic hypotension in chronic hemodialysis," Journal of the Formosan Medical Association (2018) 117, 888-893 (Year: 2018).*

(Continued)

*Primary Examiner* — Mark Holcomb
(74) *Attorney, Agent, or Firm* — Lando & Anastasi, LLP

(57) ABSTRACT

Techniques for real-time intradialytic hypotension (IDH) prediction are disclosed. A system obtains historical hemodialysis treatment data that is segmented into sets of machine learning training data based on temporal proximities to IDH events and trains a machine learning model to predict IDH events based on the sets of machine learning training data.

15 Claims, 14 Drawing Sheets

(51) Int. Cl.
*G16H 20/40* (2018.01)
*G16H 50/30* (2018.01)

(56) References Cited

U.S. PATENT DOCUMENTS

| | | | |
|---|---|---|---|
| 2010/0113891 A1 | 5/2010 | Barrett et al. | |
| 2011/0295621 A1* | 12/2011 | Farooq | G16H 50/20 |
| | | | 705/3 |
| 2012/0330117 A1 | 12/2012 | Grudic et al. | |
| 2014/0323942 A1 | 10/2014 | Atallah et al. | |
| 2015/0045713 A1 | 2/2015 | Attalah et al. | |
| 2017/0193395 A1 | 7/2017 | Limonad et al. | |
| 2017/0213145 A1* | 7/2017 | Pathak | G08B 21/0446 |
| 2017/0332922 A1* | 11/2017 | Quinn | A61B 3/165 |
| 2017/0354382 A1* | 12/2017 | Fauss | G16H 50/30 |
| 2018/0025290 A1* | 1/2018 | Al Hatib | G06N 5/04 |
| | | | 706/12 |
| 2023/0040480 A1 | 2/2023 | Urakabe | |

FOREIGN PATENT DOCUMENTS

| | | | | |
|---|---|---|---|---|
| WO | 2015179401 A1 | 11/2015 | | |
| WO | WO-2019008798 A1 * | 1/2019 | | A61B 5/412 |
| WO | 2019171015 A1 | 9/2019 | | |

OTHER PUBLICATIONS

Flythe et al., "Association of mortality risk with various definitions of intradialytic hypotension", Journal of the American Society of Nephrology, JASN vol. 26, 3 (2015), pp. 724-734.

Sands et al., "Intradialytic hypotension: frequency, sources of variation and correlation with clinical outcome", Hemodialysis International, Apr. 2014, vol. 18(2), pp. 415-422.

International Search Report and Written Opinion from corresponding International Application No. PCT/US2020/062766 dated Mar. 12, 2021.

Lin et al. "Intelligent system to predict intradialytic hypotension in chronic hemodialysis." In: Journal of the Formosan Medical Association. May 30, 2018 (May 30, 2018) Retrieved on Jan. 25, 2021 (Jan. 25, 2021) from <https://reader.elsevier.com/reader/sd/pii/ S0929664618302584token=DF8815E4813279C0955841029873DE F4A5A7EC45E925236E3D3409975838627918D8BC9FBB6E438 87F02A41241 F7D295>.

Rudin et al., "Why Are We Using Black Box Models in AI When We Don't Need To? A Lesson From an Explainable AI Competition," Harvard Data Science Review, Issue 1.2, Fall 2019.

Extended European Search Report from corresponding European Application No. 20902753.1 dated Dec. 12, 2023.

Office Action from corresponding Japanese Application No. 2022-537611 dated May 7, 2024.

* cited by examiner ions. One or more embodiments include machine learning that lacks or otherwise disregards data in a time window that immediately precedes an IDH event, for example, in the 15 minutes preceding an IDH event. Disregarding data in a time window that immediately precedes an IDH event may help the trained model predict, in real time, an IDH event with sufficient time for clinical intervention.

REAL-TIME INTRADIALYTIC HYPOTENSION PREDICTION

RELATED APPLICATIONS

This application claims the benefit of U.S. Provisional Patent Application Ser. No. 62/951,259, titled "REAL-TIME INTRADIALYTIC HYPOTENSION PREDICTION," filed Dec. 20, 2019, which is hereby incorporated by reference in its entirety.

BACKGROUND

Intradialytic hypotension (IDH) is one of the most frequent complications encountered during hemodialysis. By some estimates, IDH occurs in up to thirty percent (30%) of all hemodialysis sessions. See, e.g., Intradialytic hypotension: frequency, sources of variation and correlation with clinical outcome. Sands J J, Usvyat L A, Sullivan T, Segal J H, Zabetakis P, Kotanko P, Maddux F W, Diaz-Buxo J A. Hemodial Int. 2014 April; 18(2):415-22. doi: 10.1111/hdi.12138. Epub 2014 Jan. 27).

IDH is a major risk factor for increased morbidity and mortality. For example, IDH may lead to dizziness, vomiting, unconsciousness, and/or other complications. Managing IDH incidences requires substantial staff attention, adding to the overall cost of treatment. For these and/or other reasons, improved IDH risk management is therefore an important goal in many clinical settings. For example, the United States health care system appears to be moving toward comprehensive care models for end-stage renal disease (ESRD), in which improved IDH risk management may be highly relevant to overall treatment outcomes.

Approaches described in this section have not necessarily been conceived and/or pursued prior to the filing of this application. Accordingly, unless otherwise indicated, approaches described in this section should not be construed as prior art.

TECHNICAL FIELD

The present disclosure relates generally to predicting intradialytic hypotension.

SUMMARY

One or more embodiments improve IDH prediction over prior approaches and allow for real-time IDH prediction. One or more embodiments include machine learning using a negative class of patient data (i.e., data from a time period prior to an IDH event when the patient was below the threshold for predicting IDH) and a positive class of patient data (i.e., data from a time period prior to an IDH event when the patient was at or above the threshold for predicting IDH). Using a negative class of patient data may help the trained model differentiate, in real time, between negative and positive conditions. Using a negative class of patient data may also help prevent premature IDH predictions. One or more embodiments include machine learning using a non-IDH class of patient data (i.e., data from patients who did not experience an IDH event). Using a non-IDH class of patient data may help the trained model differentiate, in real time, between pre-IDH conditions and non-IDH conditions. One or more embodiments include machine learning that lacks or otherwise disregards data in a time window that immediately precedes an IDH event, for example, in the 15 minutes preceding an IDH event. Disregarding data in a time window that immediately precedes an IDH event may help the trained model predict, in real time, an IDH event with sufficient time for clinical intervention.

In general, in one aspect, one or more non-transitory computer-readable media store instructions that, when executed by one or more processors, cause: obtaining historical hemodialysis treatment data that is segmented into sets of machine learning training data based on temporal proximities to intradialytic hypotension (IDH) events; and training a machine learning model to predict IDH events based on the sets of machine learning training data. The sets of machine learning training data may include: a first set of machine learning training data labeled as a positive class, including medical data recorded within a minimum duration before IDH events and a maximum duration before IDH events, wherein the minimum duration is at least long enough to medically intervene before an IDH event; and a second set of machine learning training data labeled as a negative class, including medical data recorded more than the maximum duration before IDH events.

The one or more non-transitory computer-readable media may further store instructions that, when executed by one or more processors, cause: obtaining real-time hemodialysis data associated with a hemodialysis patient; and applying the real-time hemodialysis data to the machine learning model, to predict whether an IDH event is imminent for the hemodialysis patient. Based on the real-time hemodialysis data, the machine learning model may predict that the IDH event is not imminent. Based on the real-time hemodialysis data, the machine learning model may predict that the IDH event is imminent.

The one or more non-transitory computer-readable media may further store instructions that, when executed by one or more processors, cause: responsive to predicting that the IDH event is imminent, adjusting without human intervention a treatment of the hemodialysis patient to prevent the IDH event. Adjusting without human intervention the treatment of the hemodialysis patient may include one or more of reducing an ultrafiltration rate, decreasing a dialysate temperature, or mechanically repositioning the hemodialysis patient.

In general, in one aspect, a system includes at least one device including a hardware processor. The system is configured to perform operations including: obtaining historical hemodialysis treatment data that is segmented into sets of machine learning training data based on temporal proximities to intradialytic hypotension (IDH) events; and training a machine learning model to predict IDH events based on the sets of machine learning training data. The sets of machine learning training data may include: a first set of machine learning training data labeled as a positive class, including medical data recorded within a minimum duration before IDH events and a maximum duration before IDH events, wherein the minimum duration is at least long enough to medically intervene before an IDH event; and a second set of machine learning training data labeled as a negative class, including medical data recorded more than the maximum duration before IDH events.

The operations may further include: obtaining real-time hemodialysis data associated with a hemodialysis patient; and applying the real-time hemodialysis data to the machine learning model, to predict whether an IDH event is imminent for the hemodialysis patient. Based on the real-time hemodialysis data, the machine learning model may predict that the IDH event is not imminent. Based on the real-time hemodialysis data, the machine learning model may predict that the IDH event is imminent.

The operations may further include: responsive to predicting that the IDH event is imminent, adjusting without human intervention a treatment of the hemodialysis patient to prevent the IDH event. Adjusting without human intervention the treatment of the hemodialysis patient may include one or more of reducing an ultrafiltration rate, decreasing a dialysate temperature, or mechanically repositioning the hemodialysis patient.

In general, in one aspect, a method includes: obtaining historical hemodialysis treatment data that is segmented into sets of machine learning training data based on temporal proximities to intradialytic hypotension (IDH) events; and training a machine learning model to predict IDH events based on the sets of machine learning training data. The sets of machine learning training data may include: a first set of machine learning training data labeled as a positive class, including medical data recorded within a minimum duration before IDH events and a maximum duration before IDH events, wherein the minimum duration is at least long enough to medically intervene before an IDH event; and a second set of machine learning training data labeled as a negative class, including medical data recorded more than the maximum duration before IDH events.

The method may further include: obtaining real-time hemodialysis data associated with a hemodialysis patient; and applying the real-time hemodialysis data to the machine learning model, to predict whether an IDH event is imminent for the hemodialysis patient. Based on the real-time hemodialysis data, the machine learning model may predict that the IDH event is not imminent. Based on the real-time hemodialysis data, the machine learning model may predict that the IDH event is imminent.

The method may further include: responsive to predicting that the IDH event is imminent, adjusting without human intervention a treatment of the hemodialysis patient to prevent the IDH event. Adjusting without human intervention the treatment of the hemodialysis patient includes one or more of reducing an ultrafiltration rate, decreasing a dialysate temperature, or mechanically repositioning the hemodialysis patient.

One or more embodiments described in this Specification and/or recited in the claims may not be included in this General Overview section.

BRIEF DESCRIPTION OF THE DRAWINGS

Various aspects of at least one embodiment are discussed below with reference to the accompanying Figures, which are not intended to be drawn to scale. The Figures are included to provide illustration and a further understanding of the various aspects and embodiments, and are incorporated in and constitute a part of this specification, but are not intended to define the limits of the disclosure. In the Figures, each identical or nearly identical component that is illustrated in various Figures is represented by a like numeral. For the purposes of clarity, some components may not be labeled in every figure. In the Figures.

DETAILED DESCRIPTION

Figure 1:
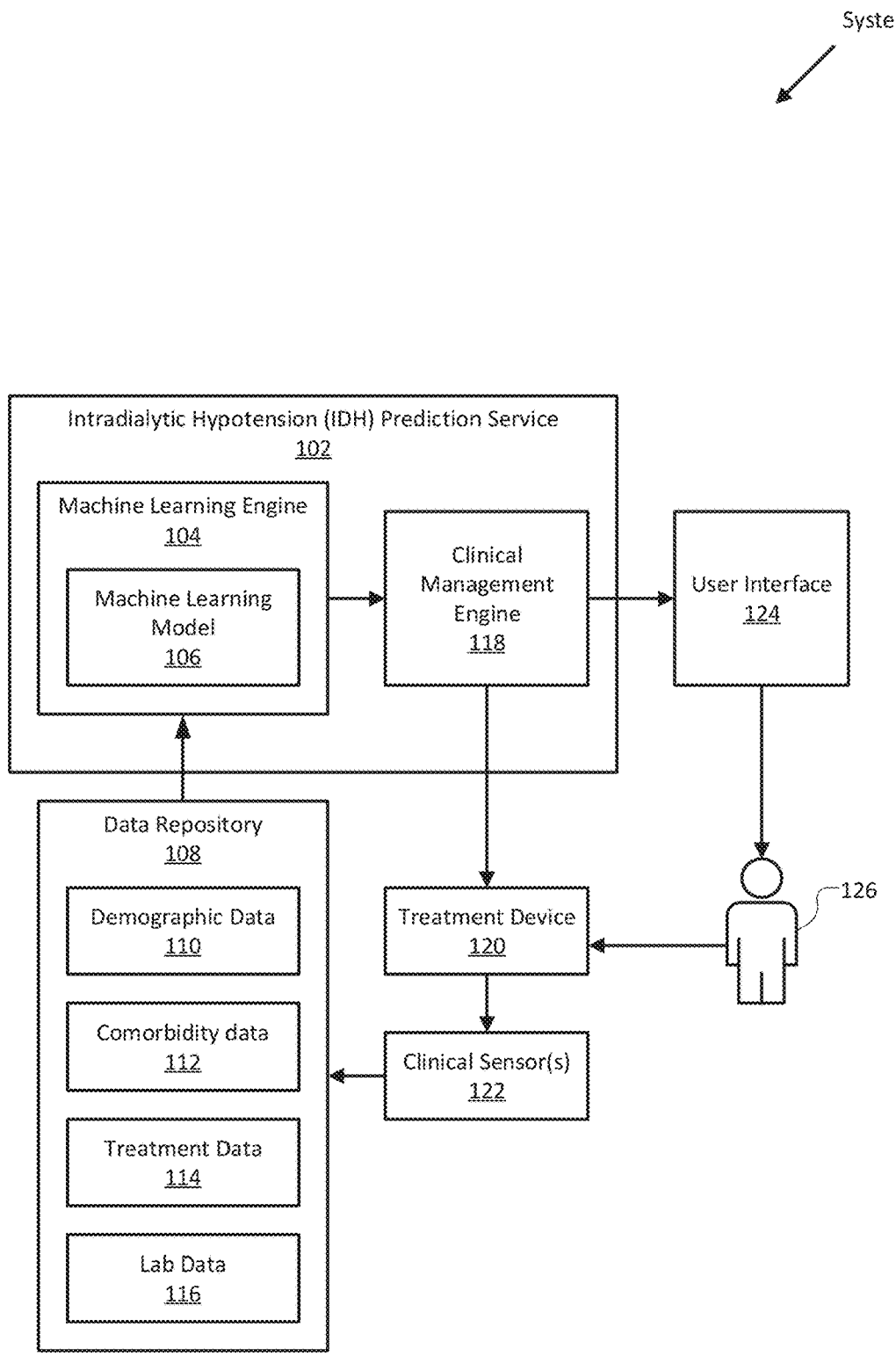
FIG. 1 is a block diagram of an example of a system according to an embodiment.

FIG. 1 is a block diagram of an example of a system 100 according to an embodiment. In an embodiment, the system 100 may include more or fewer components than the components illustrated in FIG. 1. The components illustrated in FIG. 1 may be local to or remote from each other. The components illustrated in FIG. 1 may be implemented in software and/or hardware. Each component may be distributed over multiple applications and/or machines. Multiple components may be combined into one application and/or machine. Operations described with respect to one component may instead be performed by another component.

In an embodiment, an intradialytic hypotension (IDH) prediction service 102 refers to hardware and/or software configured to perform operations for real-time IDH prediction. Examples of operations for real-time IDH prediction are described below. Specifically, the IDH prediction service 102 includes a machine learning engine 104. Machine learning includes various techniques in the field of artificial intelligence that deal with computer-implemented, user-independent processes for solving problems that have variable inputs. For example, one or more embodiments may use machine learning to predict a risk of IDH, predict an outcome of a course of treatment, recommend an alternative course of treatment, and/or provide another kind of prediction, recommendation, and/or other information based on real-time data as described herein. The machine learning engine 104 may be configured to compute a metric (e.g., a percentage, fractional value, integer value, letter grade, and/or other kind of metric or combination thereof) corresponding to the risk of an imminent IDH event. The metric may be compared (i.e., by the machine learning engine 104 and/or by another component of the system 100) and compared with one or more threshold values, as described herein.

In an embodiment, the machine learning engine 104 trains a machine learning model 106 to perform one or more operations. Training a machine learning model 106 uses training data to generate a function that, given one or more inputs to the machine learning model 106, computes a corresponding output. The output may correspond to a prediction based on prior machine learning. In an embodiment, the output includes a label, classification, and/or categorization assigned to the provided input(s). The machine learning model 106 corresponds to a learned model for performing the desired operation(s) (e.g., labeling, classifying, and/or categorizing inputs). The system 100 may use multiple machine learning engines and/or multiple machine learning models for different purposes.

In an embodiment, the machine learning engine 104 may use supervised learning, semi-supervised learning, unsupervised learning, reinforcement learning, and/or another training method or combination thereof. In supervised learning, labeled training data includes input/output pairs in which each input is labeled with a desired output (e.g., a label, classification, and/or categorization), also referred to as a supervisory signal. In semi-supervised learning, some inputs are associated with supervisory signals and other inputs are not associated with supervisory signals. In unsupervised learning, the training data does not include supervisory signals. Reinforcement learning uses a feedback system in which the machine learning engine 104 receives positive and/or negative reinforcement in the process of attempting to solve a particular problem (e.g., to optimize performance in a particular scenario, according to one or more predefined performance criteria). In an embodiment, the machine learning engine 104 initially uses supervised learning to train the machine learning model 106 and then uses unsupervised learning to update the machine learning model 106 on an ongoing basis.

In an embodiment, a machine learning engine 104 may use many different techniques to label, classify, and/or categorize inputs. A machine learning engine 104 may transform inputs into feature vectors that describe one or more properties ("features") of the inputs. The machine learning engine 104 may label, classify, and/or categorize the inputs based on the feature vectors. Alternatively or additionally, a machine learning engine 104 may use clustering (also referred to as cluster analysis) to identify commonalities in the inputs. The machine learning engine 104 may group (i.e., cluster) the inputs based on those commonalities. The machine learning engine 104 may use hierarchical clustering, k-means clustering, and/or another clustering method or combination thereof. In an embodiment, a machine learning engine 104 includes an artificial neural network. An artificial neural network includes multiple nodes (also referred to as artificial neurons) and edges between nodes. Edges may be associated with corresponding weights that represent the strengths of connections between nodes, which the machine learning engine 104 adjusts as machine learning proceeds. Alternatively or additionally, a machine learning engine 104 may include a support vector machine. A support vector machine represents inputs as vectors. The machine learning engine 104 may label, classify, and/or categorizes inputs based on the vectors. Alternatively or additionally, the machine learning engine 104 may use a naïve Bayes classifier to label, classify, and/or categorize inputs. Alternatively or additionally, given a particular input, a machine learning model 106 may apply a decision tree to predict an output for the given input. Alternatively or additionally, a machine learning engine 104 may apply fuzzy logic in situations where labeling, classifying, and/or categorizing an input among a fixed set of mutually exclusive options is impossible or impractical. The aforementioned machine learning model 106 and techniques are discussed for exemplary purposes only and should not be construed as limiting one or more embodiments.

In an embodiment, the system 100 includes a data repository 108. The data repository 108 is configured to store historical hemodialysis treatment data, i.e., data about hemodialysis patients and treatments provided to those patients. The historical hemodialysis treatment data may include demographic data 110. Alternatively or additionally, the historical hemodialysis treatment data may include comorbidity data 112. Alternatively or additionally, the historical hemodialysis treatment data may include treatment data 114. Alternatively or additionally, the historical hemodialysis treatment data may include lab data 116. In general, combined with techniques described herein, intradialytic measurements such as systolic blood pressure (SBP), diastolic blood pressure (DBP), and ultrafiltration rate may allow for previously unavailable insights into hemodynamics during hemodialysis and particularly around the time of an IDH event.

Historical hemodialysis treatment data may include, for example, data associated with one or more of: number of days from the first date of dialysis; blood flow rate; dialysis flow rate; diastolic sitting blood pressure; fluids removed; pulse; systolic sitting blood pressure; ultrafiltration rate; change in systolic blood pressure (SBP) between measurements (e.g., between a current measurement, a measurement before the current measurement during the same session, and/or a pre-treatment measurement); change in diastolic blood pressure (DBP) between measurements (e.g., between a current measurement, a measurement before the current measurement during the same session, and/or a pre-treatment measurement); change in pulse between measurements; a label or supervisory signal (e.g., positive or negative for IDH); treatment time in minutes; patient ethnicity (e.g., whether the patient is Hispanic); patient sex and/or gender; patient height; information about the dialysis access point (e.g., whether the access point is an arteriovenous (AV) fistula, AV graft, or catheter); pre-treatment SBP; pre-treatment DBP; pre-treatment weight; pre-treatment temperature; prescribed dry weight; intradialytic weight gain (e.g., in kilograms); intradialytic weight gain percentage; pre-scribed treatment time; dialysate sodium (Na); difference between serum and dialysate Na; normalized protein catabolic rate (PCR); fluid volume; delivered equilibrated eKt/V; pre-treatment urea; post-treatment urea; urea reduction ration (URR); methoxy polyethylene glycol-epoetin beta (e.g., Mircera) dose; albumin; alkaline phosphatase (ALP); basophils; bicarbonate; serum calcium; calcium corrected; chloride; creatinine; eosinophils; ferritin; hematocrit (hct); hemoglobin (hgb); lymphocytes; mean corpuscular hemoglobin (MCH); MCH concentration (MCHC); mean corpuscular volume (MCV); monocytes; neutrophils; neutrophil-lymphocyte ratio (NLR); phosphorous; platelets; potassium; red blood cell (RBC) count; RBC distribution width; serum Na; total iron binding capacity (TIBC); transferrin saturation (TSAT); information about comorbidities (e.g., whether the patient has anemia, cancer of the skin, arrhythmia, cerebrovascular disease, congestive heart failure (CHF), chronic obstructive pulmonary disease (COPD), disabilities, drug and/or alcohol dependence, gastrointestinal bleeding, hepatitis, human immunodeficiency virus (HIV)/acquired immune deficiency syndrome (AIDS), hyperparathyroidism, infection, ischemic heart disease (IHD), myocardial infarction (MI), peripheral artery disease (PAD)/percent atheroma volume (PAD), pneumonia, and/or another comorbidity); age at first date of dialysis; week day of dialysis treatment; post SBP at last treatment; post DBP at last treatment; blood flow rate (QB) at last treatment; dialysis fluid flow rate (QD) at last treatment; post-weight at last treatment; post weight gradient at last treatment; ultrafiltration volume at last treatment; ultrafiltration rate at last treatment; post temperature at last treatment; treatment time in minutes of the last treatment; treatment time gradient for the last treatment; saline used in the last treatment; online clearance (OLC) measurements; body mass index (BMI) at the last treatment; lowest SBP during the previous treatment; lowest DBP during the previous treatment; lowest pulse during the previous treatment; whether an IDH event happened during the previous treatment; a rate of IDH events over a full history of treatments; a rate of IDH events over n most recent treatments (e.g., n=10); a mean of the lowest pulse over n most recent treatments (e.g., n=10); the patient's racial identity; and/or another kind of data or combination thereof.

One or more items of historical hemodialysis treatment data may be represented as Boolean data (e.g., true/false, 0/1, yes/no, etc.). For example, Boolean data may be used to indicate whether a patient is Hispanic. Alternatively or additionally, one or more items of historical hemodialysis treatment data may be represented as a number, letter, string, or other data type. For example, measurements may be represented as numerical values.

In an embodiment, the data repository 108 is any type of storage unit and/or device (e.g., a file system, database, collection of tables, or any other storage mechanism) for storing data. A data repository 108 may include multiple different storage units and/or devices. The multiple different storage units and/or devices may or may not be of the same type or located at the same physical site. Further, a data repository 108 may be implemented or may execute on the same computing system as one or more other components of the system 100. Alternatively or additionally, a data repository 108 may be implemented or executed on a computing system separate from one or more other components of the system 100. A data repository 108 may be logically integrated with one or more other components of the system 100. Alternatively or additionally, a data repository 108 may be communicatively coupled to one or more other components of the system 100 via a direct connection or via a network. In FIG. 1, a data repository 108 is illustrated as storing various kinds of information. Some or all of this information may be implemented and/or distributed across any of the components of the system 100. However, this information is illustrated within the data repository 108 for purposes of clarity and explanation.

In an embodiment, the machine learning engine 104 is configured to train the machine learning model 106 based on data stored in the data repository 108. As described in further detail below, the data may be segmented into sets of training data. Sets of training data may also be referred to as "classes," because they share one or more classification criteria. Each set may be labeled to indicate whether the data should be considered predictive of an IDH event. Specifically, the training data may be segmented into a "positive" class (i.e., to be treated as predictive of an IDH event) and a "negative" class (i.e., to be treated as not predictive of an IDH event). As described below, the data may be segmented according to temporal proximity to a recorded IDH event. Alternatively or additionally, data may be segmented into different sets of training data according to whether the data was obtained during a treatment session that included an IDH event. For example, data that was obtained during a treatment session in which no IDH event occurred may be placed in a "negative" class (i.e., the same class or a different class). Data that precedes an IDH event within a predefined time margin (e.g., 15 minutes) may be disregarded, to help ensure that predictions are based on circumstances that still allow enough time for a clinical intervention. Data recorded after an IDH event may also be disregarded.

In an embodiment, the system 100 is configured to obtain real-time hemodialysis treatment data from a hemodialysis patient 126. A treatment device 120 is configured to provide hemodialysis treatment to the patient 126. One or more clinical sensors 122 (e.g., blood pressure monitors, heartrate monitors, thermometers, etc.) may record real-time data associated with the treatment. The real-time data may be stored in the data repository 108 and/or transmitted to the IDH prediction service 102, to predict whether an IDH event is imminent for the patient 126. Alternatively or additionally, the prediction may be based on other data about the patient 126 and/or treatment, such as data obtained from a connected health system as described below.

In an embodiment, the IDH prediction service 102 is configured to predict IDH events based on threshold probabilities. Specifically, given a set of real-time input data, the IDH prediction service 102 may determine a predicted probability of an imminent IDH event. The IDH prediction service 102 may store one or more probability thresholds (not shown), which may be hard-coded or user-configurable. If the probability of an IDH event exceeds a probability threshold (or matches the probability threshold, if the value is programmed to be inclusive; or is below the threshold if lower values correspond to higher probabilities), then the IDH prediction service 102 indicates that an IDH event is predicted, i.e., likely to occur imminently. Otherwise, the IDH prediction service 102 either takes no action or indicates that no IDH event is predicted. The IDH prediction service 102 may store multiple thresholds, so that different remedial actions may be taken based on the relative severity of the patient 126's situation (i.e., more extreme actions may be taken as the probability of an imminent IDH event increases).

In an embodiment, a higher threshold value may result in more false negatives, and a lower threshold value may result in more false positives. Various techniques may be used to determine the threshold value. For example, the system 100 may compute a Youden index or a cost function that is minimized or maximized depending on the nature of the function. A threshold value may be individualized and apply only to a single patient 126, based on that particular patient 126's data (e.g., demographics, biological measurements, etc.). Alternatively, a threshold value may apply to multiple patients having one or more data properties in common (e.g., demographics, biological measurements, etc.). Alternatively, a threshold value may apply to all patients. Machine learning may be used to compute one or more threshold values for individual patients and/or one or more groups of patients.

In an embodiment, when the IDH prediction service 102 predicts that an IDH event is imminent (e.g., when the patient 126's IDH risk classification reaches a threshold value), the system 100 may generate an alert and/or adjust the patient 126's treatment to prevent the IDH event. A clinical management engine 118 refers to hardware and/or software configured to perform operations for generating an alert and/or adjusting the patient 126's treatment. An alert may be visual and/or auditory. The clinical management engine 118 may be configured to generate a recommendation for adjusting the patient 126's treatment and display the recommendation in a user interface 124. As described above, the machine learning engine 104 may be configured to generate the recommended adjustment. Alternatively or additionally, the clinical management engine 118 may be configured to generate the recommendation without machine learning, e.g., based on codified best practices.

In an embodiment, responsive to an alert (which may or may not include a recommended course of action), a clinician may inspect the patient 126, take additional measurements, and/or adjust the patient 126's course of treatment. For example, the clinician may adjust (e.g., decrease or stop) the patient 126's ultrafiltration rate, modify the dialysate temperature (e.g., decrease the temperature, which has been shown to be associated with a lower IDH rate), and/or otherwise adjust the dialysis treatment. Alternatively or additionally, the clinician may reposition the patient 126 in a manner that decreases the likelihood of the IDH event actually occurring (e.g., by raising a footrest of a dialysis chair and/or otherwise adjusting the angle of a bed or chair in which the patient 126 is situated).

In an embodiment, when the IDH prediction service 102 predicts that an IDH event is imminent, the system 100 may take action automatically, i.e., without human intervention. The system may take action to inspect the patient 126, take additional measurements, and/or adjust the patient 126's course of treatment responsive to the alert condition, without requiring intervention by a human clinician. The clinical management engine 118 may be configured to transmit instructions to a treatment device 120 and/or one or more other apparatuses, to automatically adjust the patient 126's treatment. For example, the clinical management engine 118 may transmit instructions to a hemodialysis machine to adjust the patient 126's ultrafiltration rate, modify the dialysate temperature, and/or otherwise adjust the dialysis treatment. Alternatively or additionally, the clinical management engine 118 may transmit instructions to a bed or chair in which the patient 126 is situated, to reposition the patient 126. Data from the clinical sensor(s) 122 and/or an outcome of adjusting the patient 126's treatment may be stored in the data repository 108 and/or transmitted to the machine learning engine 104, to update the machine learning model 106 based on the results.

In an embodiment, a user interface 124 refers to hardware and/or software configured to facilitate communications between a user (e.g., the patient 126 and/or a medical professional) and the IDH prediction service 102. A user interface 124 renders user interface elements and receives input via user interface elements. A user interface 124 may be a graphical user interface (GUI), a command line interface (CLI), a haptic interface, a voice command interface, and/or any other kind of interface or combination thereof. Examples of user interface elements include checkboxes, radio buttons, dropdown lists, list boxes, buttons, toggles, text fields, date and time selectors, command lines, sliders, pages, and forms.

In an embodiment, different components of a user interface 124 are specified in different languages. The behavior of user interface elements may be specified in a dynamic programming language, such as JavaScript. The content of user interface elements may be specified in a markup language, such as hypertext markup language (HTML), Extensible Markup Language (XML), or XML User Interface Language (XUL). The layout of user interface elements may be specified in a style sheet language, such as Cascading Style Sheets (CSS). Alternatively or additionally, aspects of a user interface 124 may be specified in one or more other languages, such as Java, Python, Perl, C, C++, and/or any other language or combination thereof.

In an embodiment, one or more components of the system 100 are implemented on one or more digital devices. The term "digital device" generally refers to any hardware device that includes a processor. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a hardware router, a hardware switch, a hardware firewall, a hardware network address translator (NAT), a hardware load balancer, a mainframe, a television, a content receiver, a set-top box, a printer, a mobile handset, a smartphone, a personal digital assistant ("PDA"), a wireless receiver and/or transmitter, a base station, a communication management device, a router, a switch, a controller, an access point, and/or a client device.

Figure 2:
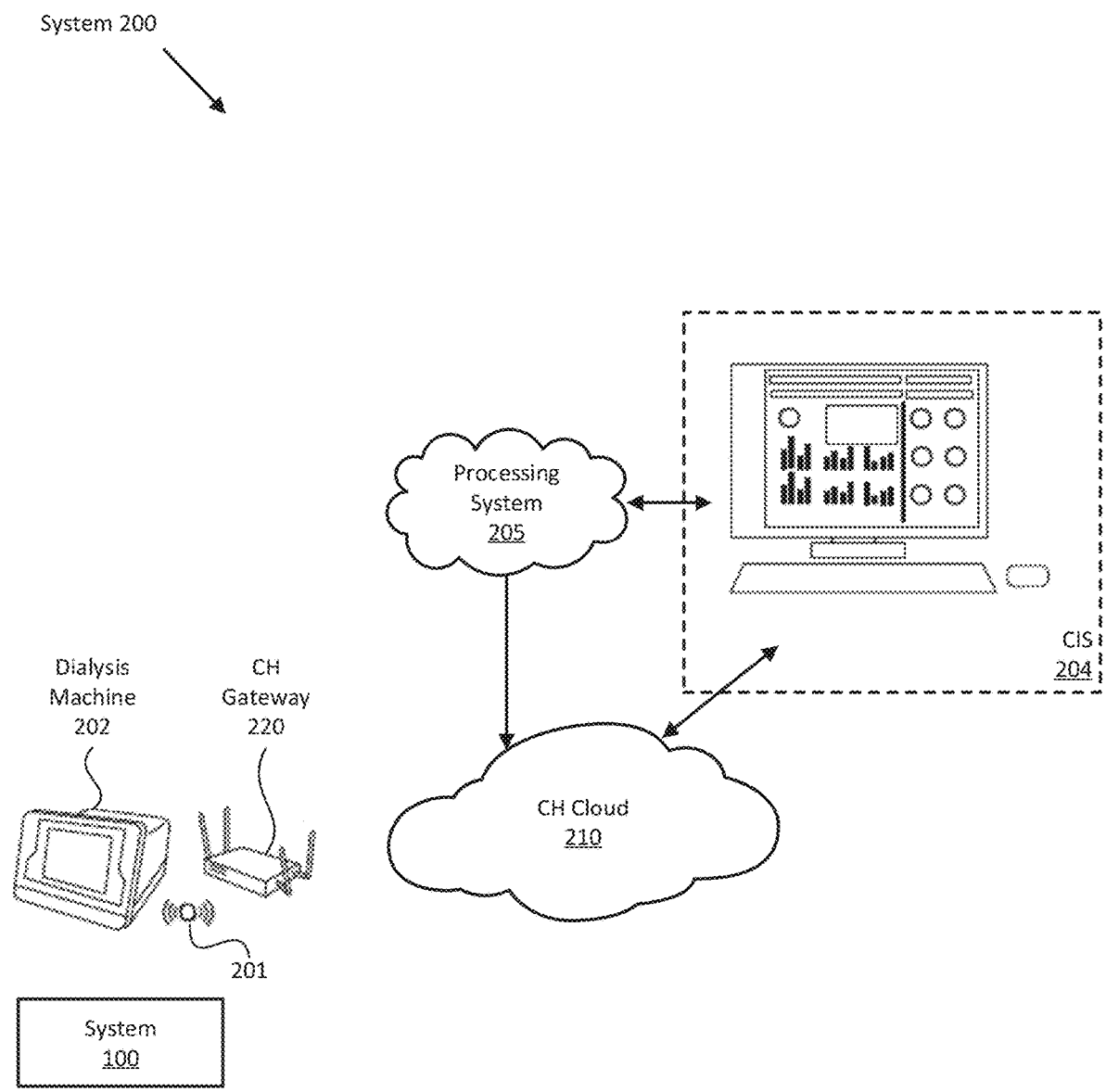
FIG. 2 is a block diagram of an example of a connected health system according to an embodiment.

FIG. 2 is a block diagram of an example of a connected health (CH) system 200 according to an embodiment. In an embodiment, the CH system 200 may include more or fewer components than the components illustrated in FIG. 2. The components illustrated in FIG. 2 may be local to or remote from each other. The components illustrated in FIG. 2 may be implemented in software and/or hardware. Each component may be distributed over multiple applications and/or machines. Multiple components may be combined into one application and/or machine. Operations described with respect to one component may instead be performed by another component.

The CH system 200 may be configured to be part of or communicate with a system such as system 100 of FIG. 1. The CH system 200 may include, among other things, a processing system 205, a CH cloud service 210, and a gateway (CH Gateway) 220 that may be used in connection with network aspects of one or more systems described herein. The processing system 205 may include a server and/or cloud-based system that processes, compatibility-checks, and/or formats medical information, including prescription information generated at a clinical information system (CIS) 204 of a clinic or hospital, in connection with data transmission operations of the CH system 200. The CH system 200 may include appropriate encryption and data security mechanisms. The CH cloud service 210 may include a cloud-based application that serves as a communication pipeline (e.g., facilitates the transfer of data) among components of the CH system 200, via connections to a network such as the Internet. The gateway 220 may serve as a communication device that facilitates communication among components of the CH system 200. In various embodiments, the gateway 220 may be in communication with a dialysis machine 202 (e.g., a peritoneal dialysis machine or hemodialysis machine) and a system 100 via a wireless connection 201, such as a Bluetooth, Wi-Fi and/or other appropriate type of local or short-range wireless connection. The gateway 220 may also be in connection with the CH cloud service 210 via a secure network (e.g. Internet) connection. The gateway 220 may be configured to transmit/receive data to/from the CH cloud service 210 and transmit/receive data to/from the dialysis machine 202 and system 100. The dialysis machine 202 may poll the CH cloud service 210 for available files (e.g., via the gateway 320), and the dialysis machine 202 and/or system 100 may temporarily store available files for processing.

Figure 3:
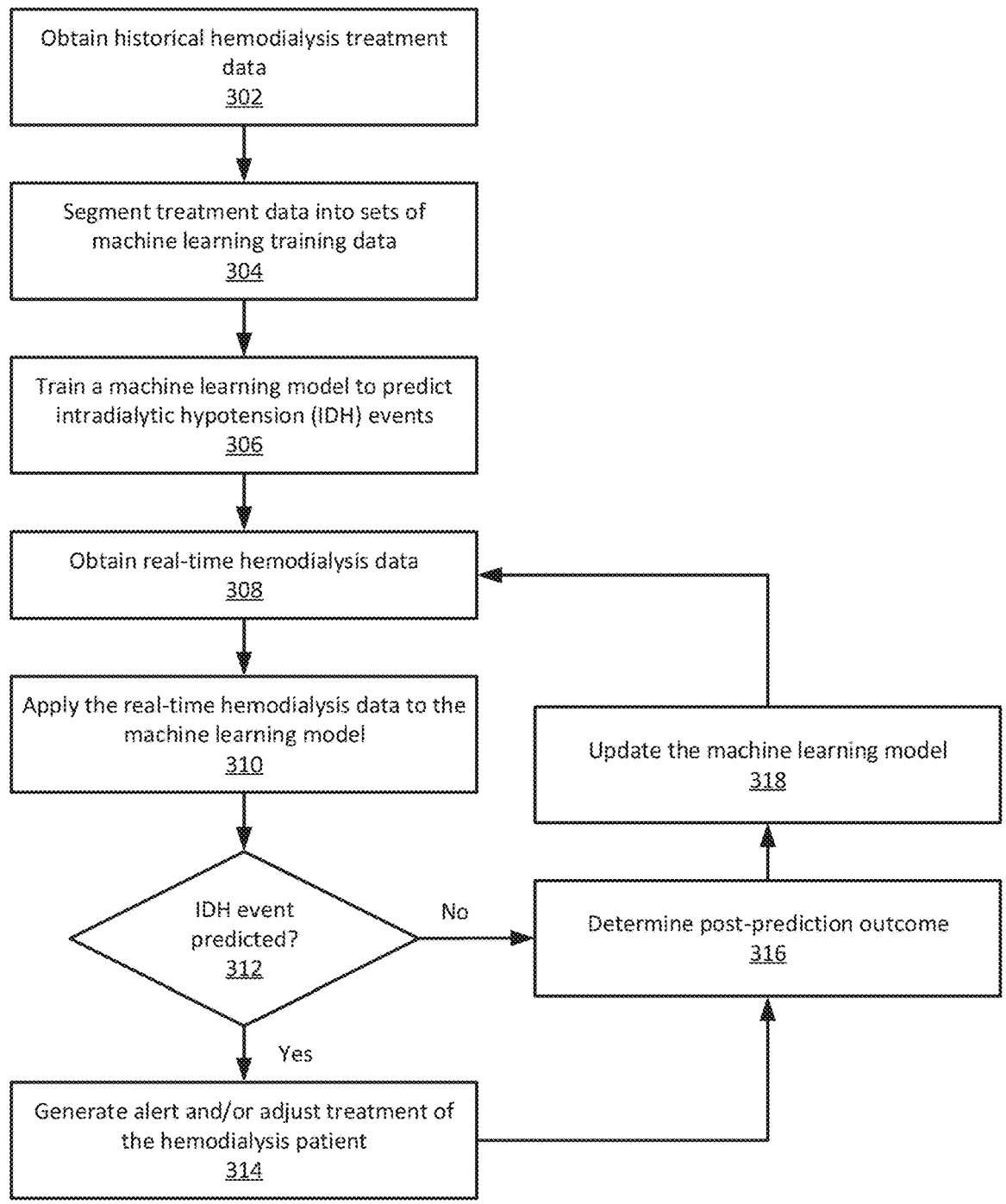
FIG. 3 is a flow diagram of an example of operations for real-time intradialytic hypotension prediction according to an embodiment.

FIG. 3 is a flow diagram of an example of operations for real-time IDH prediction according to an embodiment. One or more operations illustrated in FIG. 3 may be modified, rearranged, or omitted all together. Accordingly, the particular sequence of operations illustrated in FIG. 3 should not be construed as limiting the scope of one or more embodiments.

In an embodiment, a system (e.g., system 100 of FIG. 1) obtains historical hemodialysis treatment data (Operation 302). The system may obtain the treatment data from many different sources. For example, the system may obtain the treatment data from a connected health system as described above. Alternatively or additionally, the system may obtain the data from a third-party medical records source, such as a source that provides medical data for research, data mining, etc. Embodiments should not be considered limited to any specific data source.

In an embodiment, the system segments the treatment data into sets of machine learning training data (Operation 304), or "classes," based on one or more shared criteria.

Specifically, the training data may be segmented into a "positive" class (i.e., to be treated as predictive of an IDH event) and a "negative" class (i.e., to be treated as not predictive of an IDH event). As described below, the data may be segmented according to temporal proximity to a recorded IDH event. Alternatively or additionally, data may be segmented into different sets of training data according to whether the data was obtained during a treatment session that included an IDH event. For example, data that was obtained during a treatment session in which no IDH event occurred may be placed in a "negative" class (i.e., the same class or a different class). Data that precedes an IDH event within a predefined time margin (e.g., 15 minutes) may be disregarded, to help ensure that predictions are based on circumstances that still allow enough time for a clinical intervention. Data recorded after an IDH event may also be disregarded. Alternatively or additionally, the system may receive data that is already segmented into sets of machine learning training data, without the system needing to perform the segmentation itself.

In an embodiment, the system trains a machine learning model to predict IDH events (Operation 306), based on the segmented machine learning training data. Techniques for training a machine learning model are described in further detail above.

In an embodiment, the system obtains real-time hemodialysis data (Operation 308). Specifically, the system obtains data from one or more clinical sensor(s) that is/are monitoring the treatment of a hemodialysis patient. The system may also obtain other data associated with the patient, such as demographic data, etc. In general, the system may obtain data that corresponds to data used to train the machine learning model, and which may therefore be predictive (either alone or in combination with other data) of an IDH event.

In an embodiment, the system applies the real-time hemodialysis data to the machine learning model (Operation 310). Based on the real-time hemodialysis data, the machine learning model determines whether an IDH event is predicted (Decision 312), i.e., whether the real-time hemodialysis data indicates that the an IDH event is imminent for the patient. As discussed above, the system may predict IDH events based on threshold probabilities. Specifically, given a set of real-time input data, the system may determine a predicted probability of an imminent IDH event. If the probability of an IDH event exceeds the probability threshold (or matches the probability threshold, if the value is programmed to be inclusive; or is below the threshold if lower values correspond to higher probabilities), then the system indicates that an IDH event is predicted. Otherwise, the system either takes no action or indicates that no IDH event is predicted. The system may store multiple thresholds, so that different remedial actions may be taken based on the relative severity of the patient's situation (i.e., more extreme actions may be taken as the probability of an imminent IDH event increases).

In an embodiment, if an IDH event is predicted, then the system responds by generating an alert and/or adjusting treatment of the hemodialysis patient (Operation 314). The system may determine an adjustment using machine learning. The system may use the same machine learning model used to predict the IDH event or another machine learning model. The adjustment may be based on some or all of the same data used to predict the IDH event, and/or other data that was not used to predict the IDH event. Alternatively or additionally, the system may determine the adjustment using codified best practices (e.g., a codified decision tree based on a clinical decision-making process that might be performed by a medical professional). The system may raise a visual and/or audible alert. The alert may present a recommended adjustment in a user interface, for a human operator (e.g., the patient and/or a medical professional) to act on. Alternatively or additionally, the system may automatically perform the adjustment, for example, by transmitting instructions to an apparatus (e.g., to adjust an ultrafiltration rate, modify the dialysate temperature, reposition the patient, and/or adjust the patient's treatment in some other way).

In an embodiment, the system determines a post-prediction outcome (Operation 316). The system may determine the post-prediction outcome whether or not an IDH event was predicted and whether or not the hemodialysis patient's treatment was adjusted. In general, a post-prediction outcome may refer to real-time hemodialysis data gathered after the time when the prediction was made. The system may update the machine learning model (Operation 318) based on the post-prediction outcome. In some examples, the system obtains real-time data and updates the machine learning model on an ongoing basis (e.g., using unsupervised learning), whether or not an IDH event is predicted or actually occurs.

For purposes of clarity, some detailed examples are described below. Components and/or operations described below should be understood as examples that may not be applicable to one or more embodiments. Accordingly, components and/or operations described below should not be construed as limiting the scope of one or more embodiments.

In one example, IDH was defined as an intradialytic systolic blood pressure (SBP) below 90 mmHg. (Additional IDH definitions are described in Flythe, Jennifer E et al. "Association of mortality risk with various definitions of intradialytic hypotension." *Journal of the American Society of Nephrology: JASN* vol. 26, 3 (2015), incorporated herein by reference in its entirety.) Two data sources were used to predict IDH:

1) Pre-treatment data including demographic data, routine dialysis-specific measurements, lab values, and comorbidities; and
2) Intradialytic clinical data documented in the Chairside Information System produced by Fresenius Medical Care, including intradialytic blood pressures, intradialytic heart rate, and intradialytic ultrafiltration rates.

Static data included demographics and comorbidities, treatment data, and lab values. Intradialytic chairside data provided additional dynamic and static data. Multiple features were engineered based on the measured information (e.g., through averaging and other mathematical functions based on measured values).

Historical hemodialysis data for 2,628 patients over 332,591 treatments was obtained. 80% of the historical data was used to train a machine learning model. Specifically, in this example, the open source software XGBoost was used. Other examples may use different machine learning software and/or techniques. The remaining 20% of the historical data treated as real-time data for research purposes and applied to the machine learning model, to evaluate the model's predictive capabilities. Specifically, IDH predictions were made every time intradialytic SBP was measured (usually about every 20-30 minutes). The minimum time margin before an IDH event (i.e., the pre-IDH time margin in which data was disregarded) was set at 15 minutes; this time margin was considered sufficient to deploy preventative measures if an IDH event was predicted to be imminent.

Figure 4A:
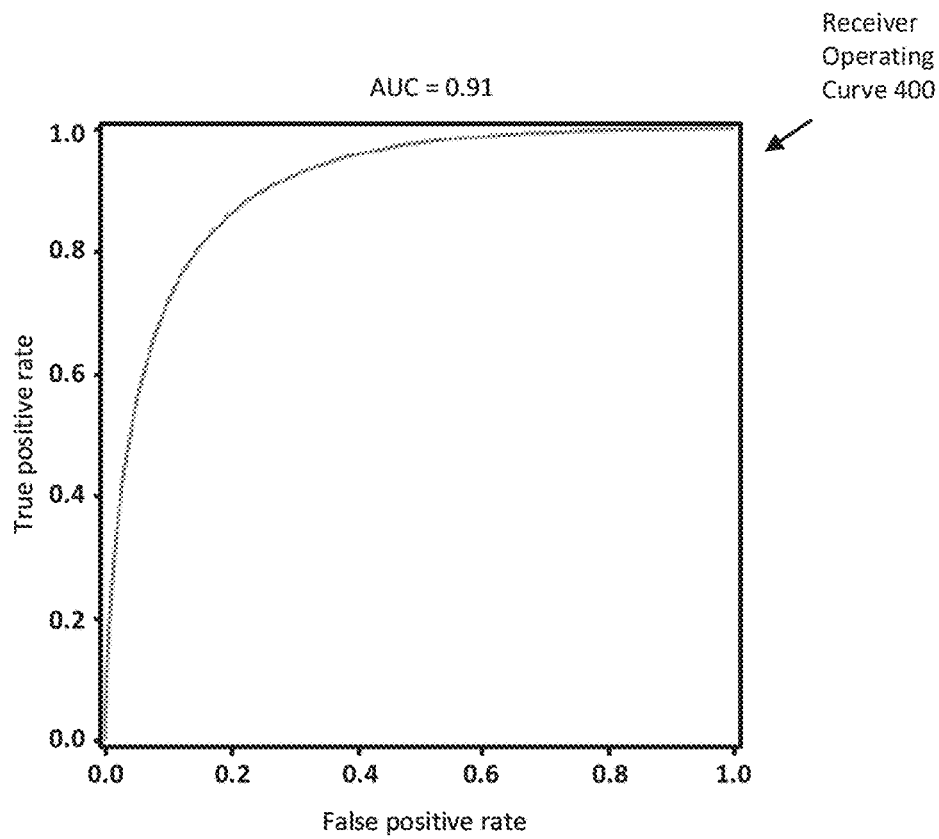
FIGS. 4A-4B illustrate examples of receiver operating curves according to an embodiment.
Figure 4A:
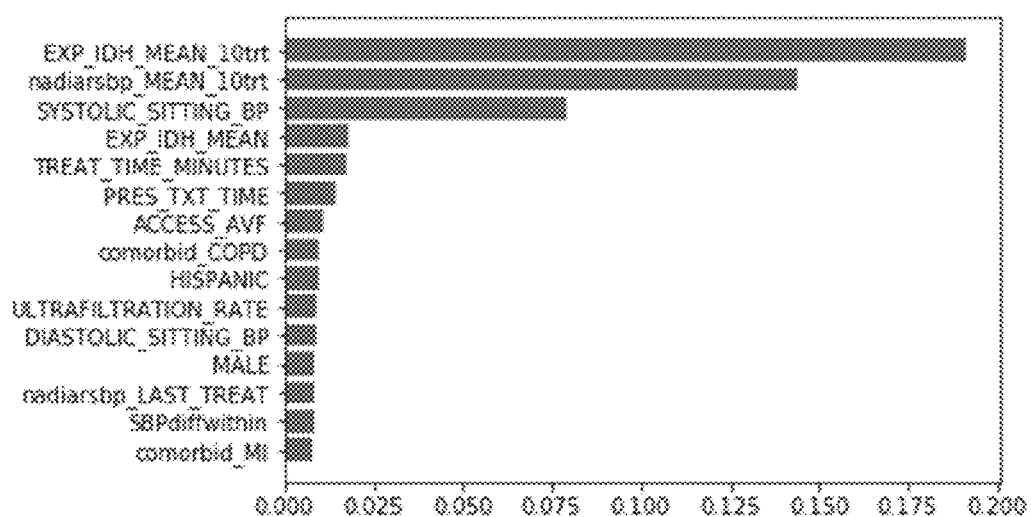
Figure 4B:
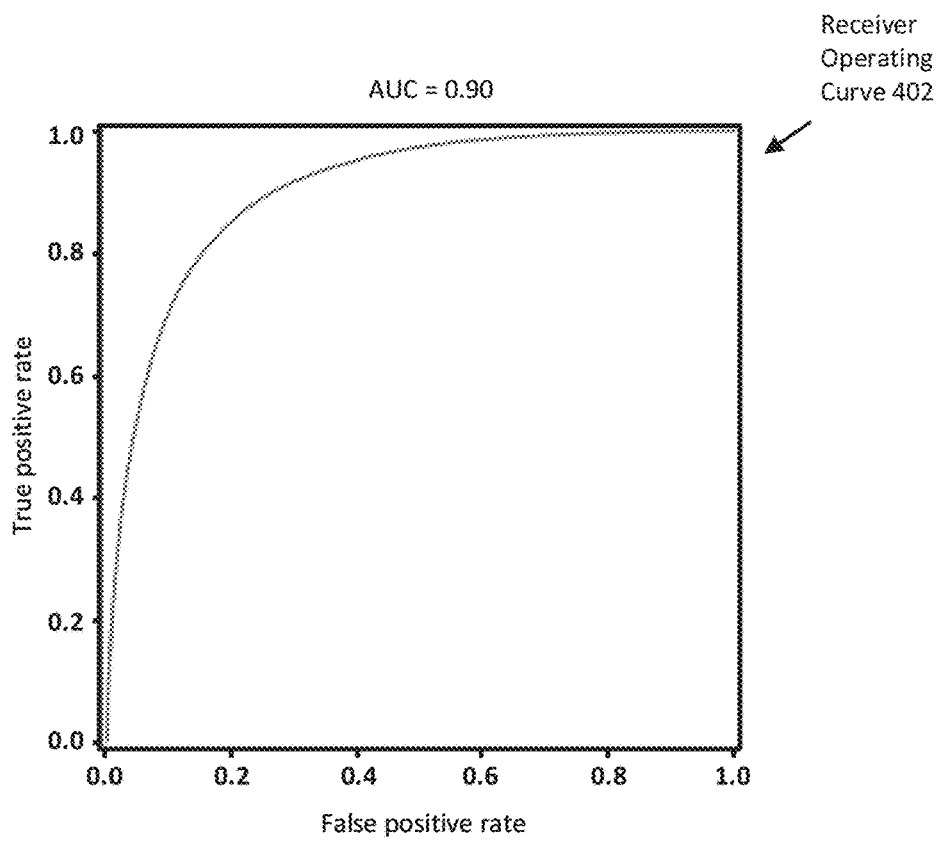
Figure 4B:
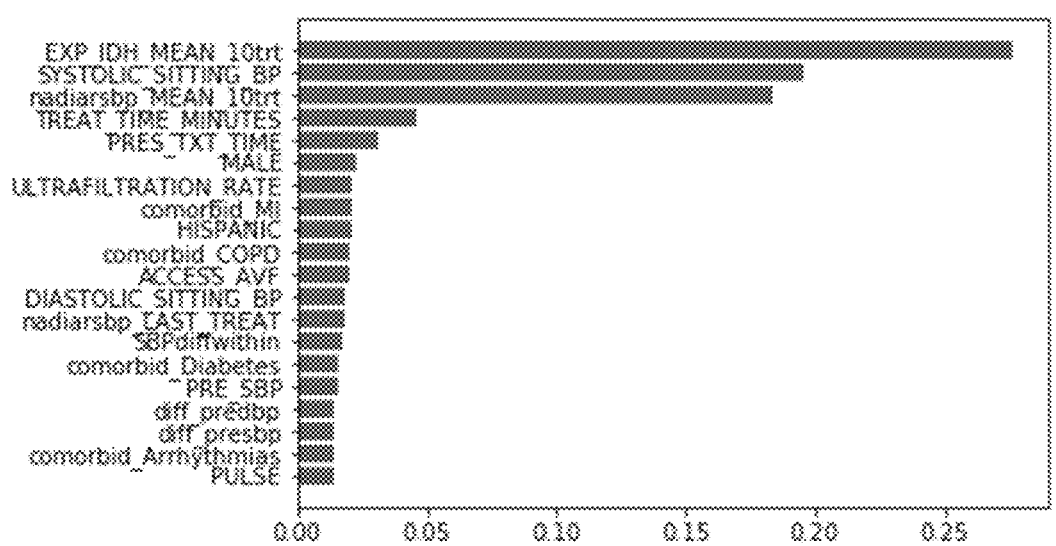

As illustrated in FIG. 4A, when the machine learning model was trained using 106 features, the receiver operating curve 400 had an area under the curve (AUC) greater than 0.9 (specifically, 0.91), indicating clinically acceptable sensitivity and specificity of IDH prediction, with a clinically acceptable false positive rate. As illustrated in FIG. 4B, even when the machine learning model was trained using only 20 features, the receiver operating curve 402 still had an AUC of 0.9. In FIGS. 4A and 4B, the charts indicate, for each model, the relative importance (i.e., experimentally determined predictive value) of each factor shown in the charts.

Figure 5:
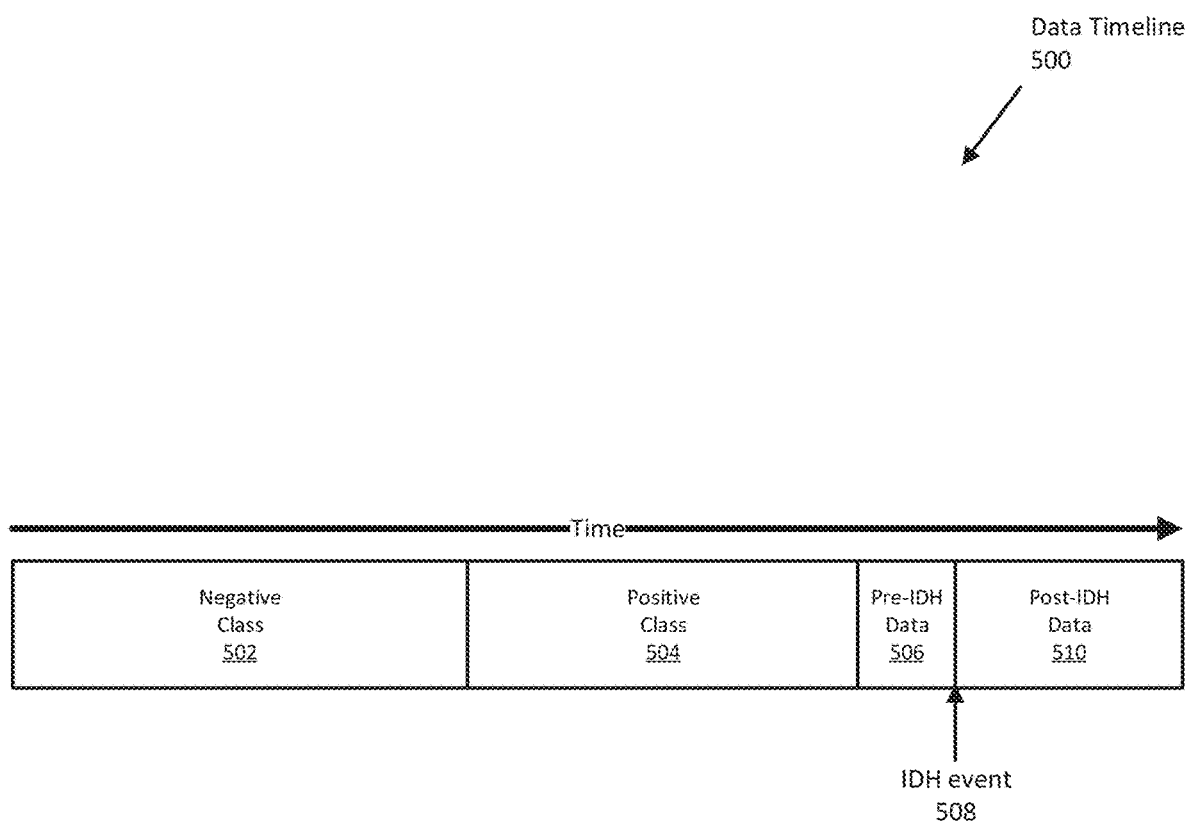
FIG. 5 is a block diagram of an example of machine learning training data sets according to an embodiment.

FIG. 5 is a block diagram of an example of machine learning training data sets according to an embodiment. As illustrated in FIG. 5, data may be segmented into training classes or disregarded based on where the data lies on a conceptual data timeline 500, i.e., in temporal relation to a recorded IDH event 508. Specifically, pre-IDH data 506 that precedes the IDH event 508 within a particular time interval (e.g., 15 minutes or another time interval) may be disregarded for machine learning purposes. Data that is older than the pre-IDH data 506 and still falls within a predefined period of time before the IDH event 508 (e.g., from 75 minutes pre-IDH to 15 minutes pre-IDH) may be segmented into a "positive" class 504. The positive class 504 corresponds to the preferred time period for predicting the IDH event 508, when there is likely to be sufficient data to determine that the DH event 508 is imminent and still enough time to intervene to prevent the IDH event. Data that is any older (e.g., more than 75 minutes before the IDH event 508) may be segmented into a negative class 502. Post-IDH data 510 may be disregarded.

Figure 6:
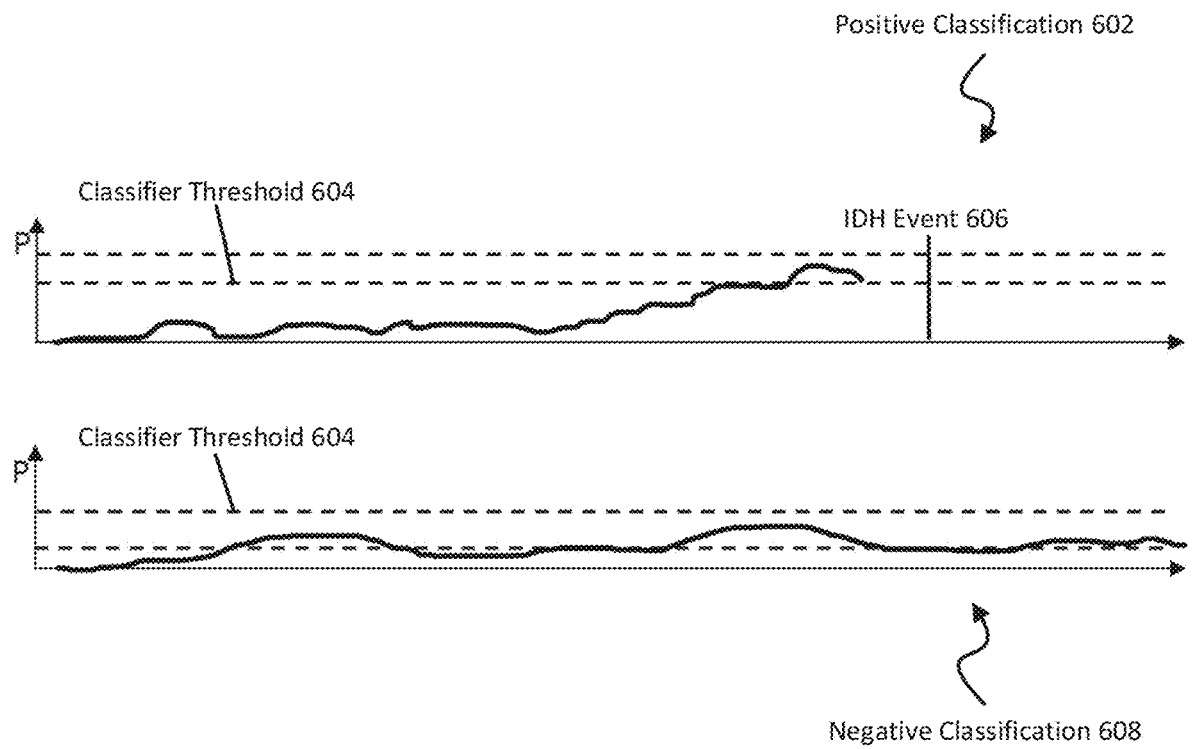
FIG. 6 illustrates an example of threshold-based classification according to an embodiment.
Figure 7A:
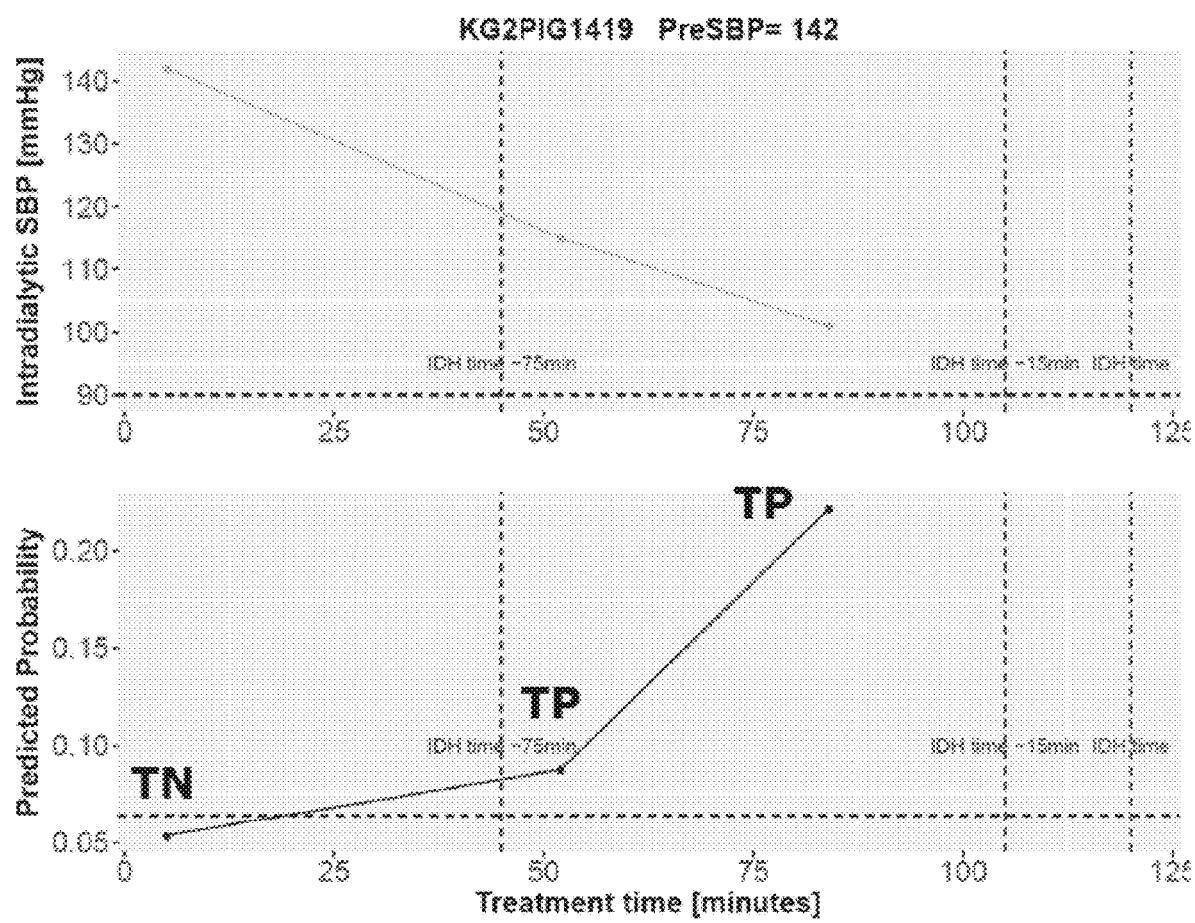
FIGS. 7A-7F illustrate examples of experimental results according to an embodiment.
Figure 7B:
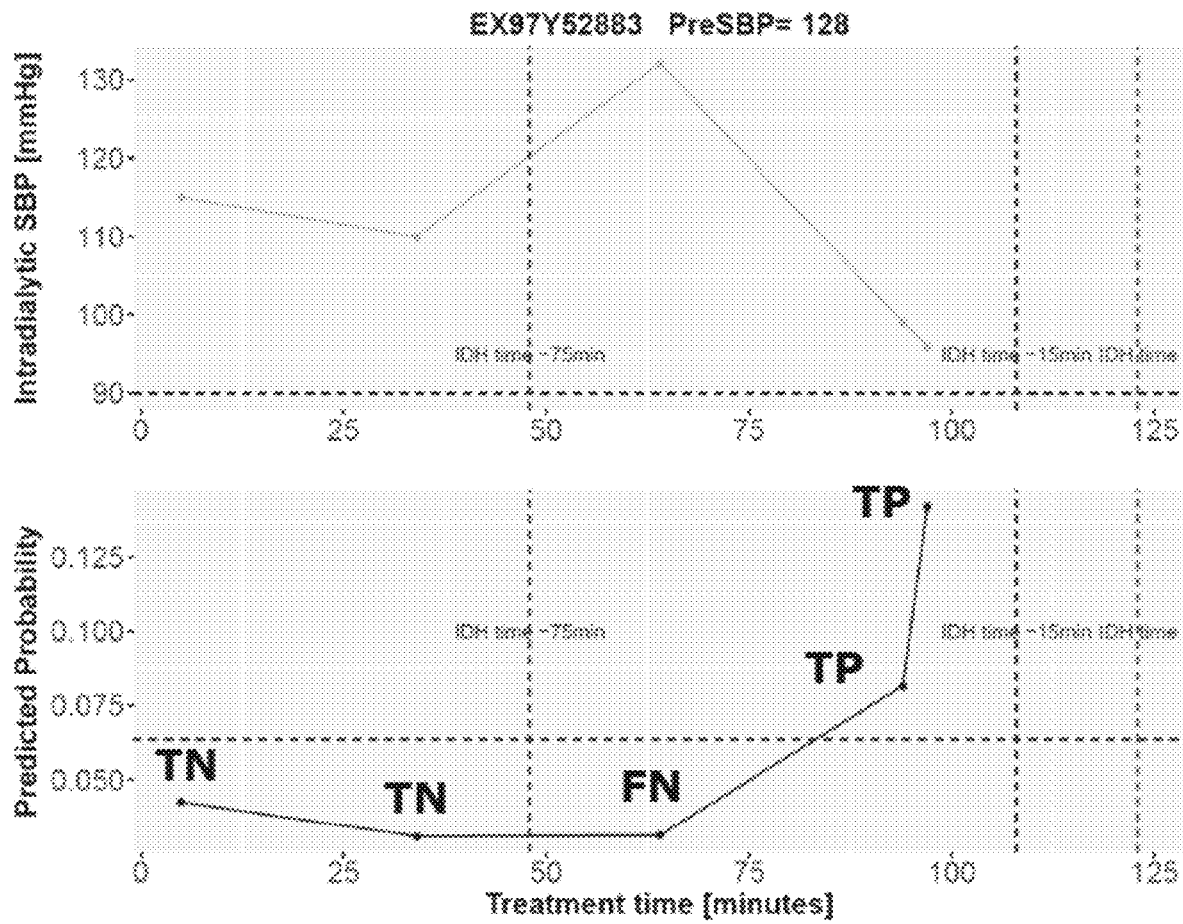
Figure 7C:
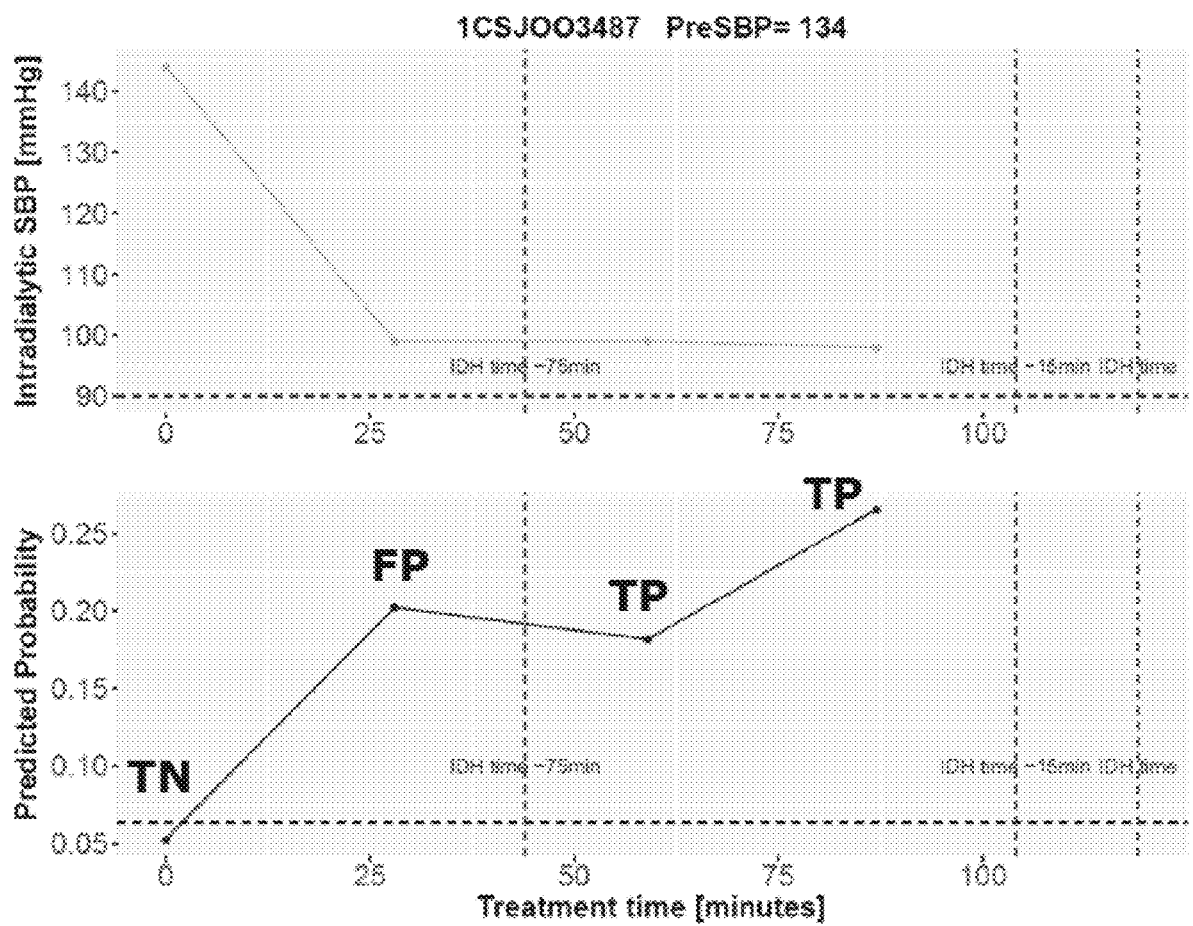
Figure 7D:
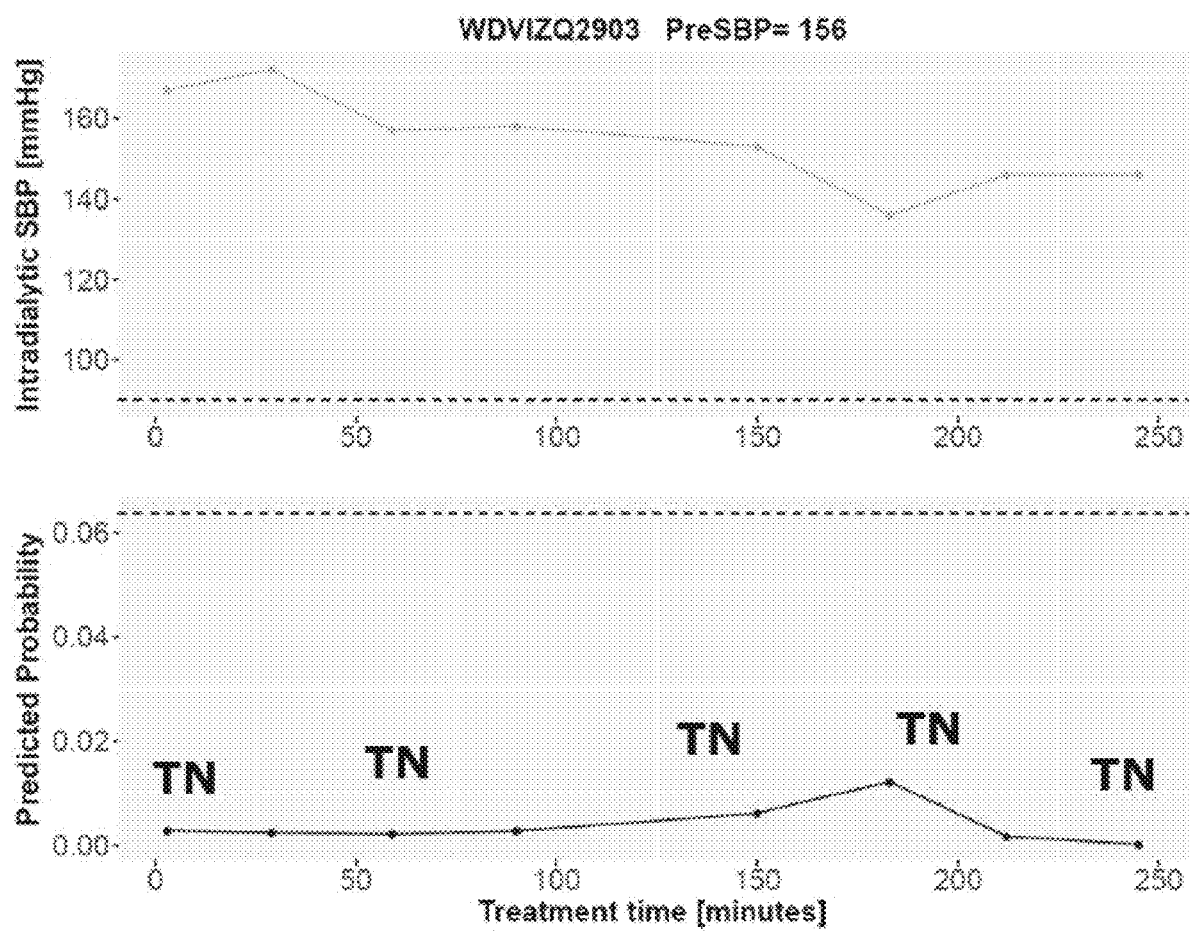
Figure 7E:
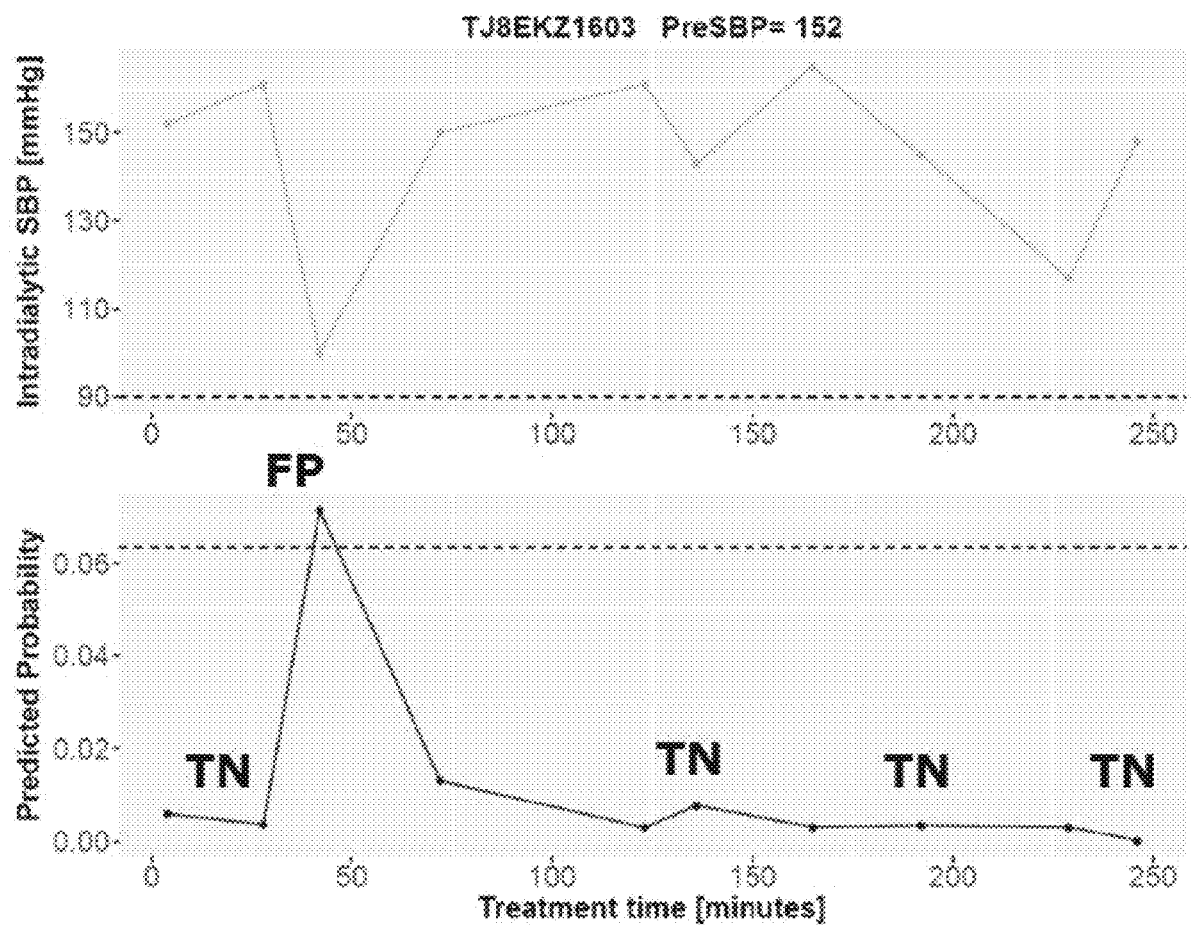
Figure 7F:
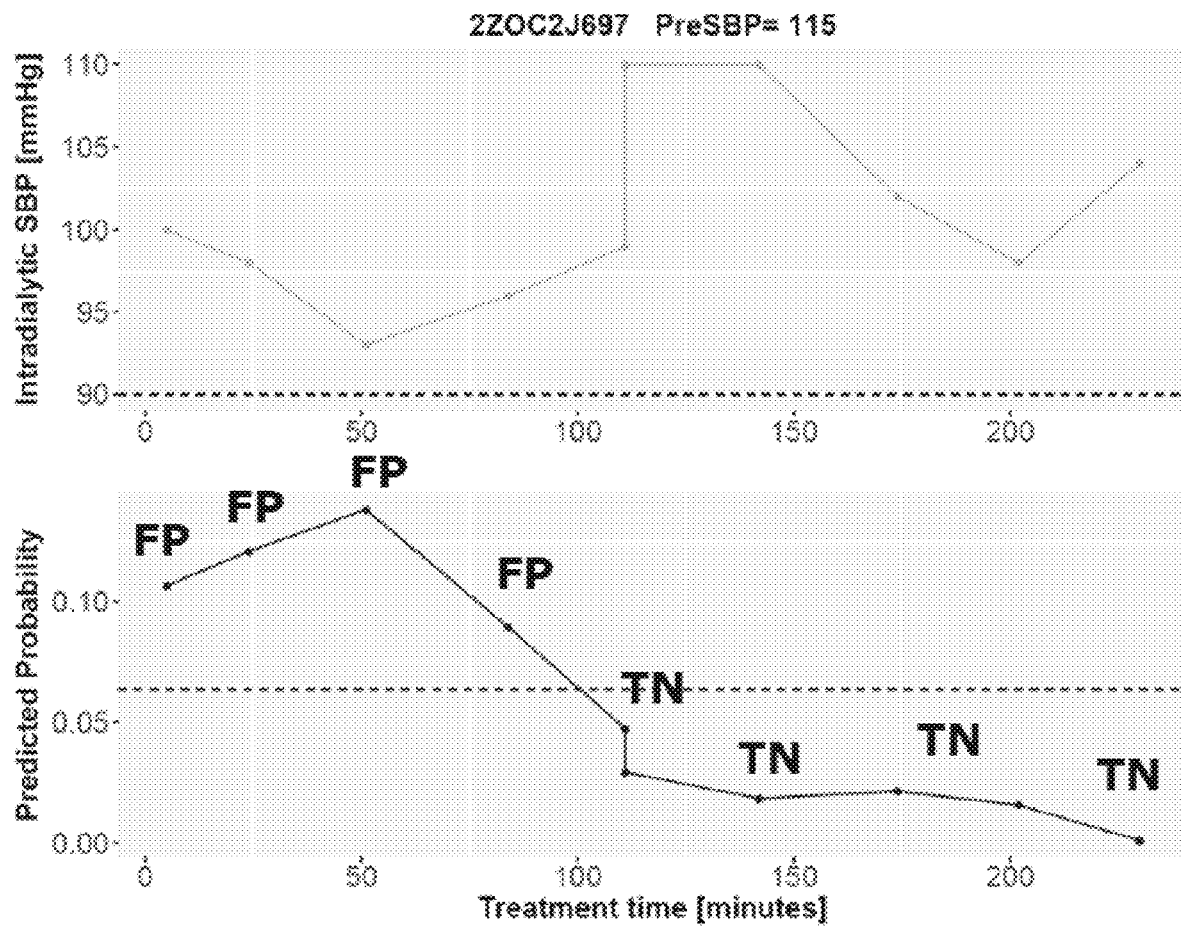

FIG. 6 illustrates an example of threshold-based classification according to an embodiment. As illustrated in FIG. 6, positive classification 602 occurs when the probability of a IDH event 606 exceeds (or in some examples, meets) a classifier threshold 604. In the example of positive classification 602, the higher dashed line illustrates how setting the classifier threshold 604 too high may result in a false negative. A negative classification 608 occurs when no IDH event occurs (as illustrated in FIG. 6) and/or the probability of an IDH event does not reach a sufficiently high threshold. In the example of negative classification 608, the lower dashed line illustrates how setting the classifier threshold 604 too low may result in a false positive.

FIGS. 7A-7F illustrate examples of experimental results according to an embodiment. In these examples, "TP" refers to a true positive result (i.e., a positive predictive classification where an IDH event actually occurred), "TN" refers to a true negative result (i.e., a negative predictive classification where no IDH event actually occurred), "FP" refers to a false positive result (i.e., a positive predictive classification where no IDH event actually occurred), and "FN" refers to a false negative result (i.e., a negative predictive classification where an IDH event actually occurred).

In an embodiment, a system includes one or more devices, including one or more hardware processors, that are configured to perform any of the operations described herein and/or recited in any of the claims.

In an embodiment, one or more non-transitory computer-readable storage media store instructions that, when executed by one or more hardware processors, cause performance of any of the operations described herein and/or recited in any of the claims.

Any combination of the features and functionalities described herein may be used in accordance with an embodiment. In the foregoing specification, embodiments have been described with reference to numerous specific details that may vary from implementation to implementation. Accordingly, the specification and figures are to be regarded in an illustrative rather than a restrictive sense. The sole and exclusive indicator of the scope of the invention, and what is intended by the Applicant to be the scope of the invention, is the literal and equivalent scope of the set of claims that issue from this application, in the specific form in which such claims issue, including any subsequent correction.

In an embodiment, techniques described herein are implemented by one or more special-purpose computing devices (i.e., computing devices specially configured to perform certain functionality). The special-purpose computing device(s) may be hard-wired to perform the techniques and/or may include digital electronic devices such as one or more application-specific integrated circuits (ASICs), field programmable gate arrays (FPGAs), and/or network processing units (NPUs) that are persistently programmed to perform the techniques. Alternatively or additionally, a computing device may include one or more general-purpose hardware processors programmed to perform the techniques pursuant to program instructions in firmware, memory, and/or other storage. Alternatively or additionally, a special-purpose computing device may combine custom hard-wired logic, ASICs, FPGAs, or NPUs with custom programming to accomplish the techniques. A special-purpose computing device may include a desktop computer system, portable computer system, handheld device, networking device, and/or any other device(s) incorporating hard-wired and/or program logic to implement the techniques.

Figure 8:
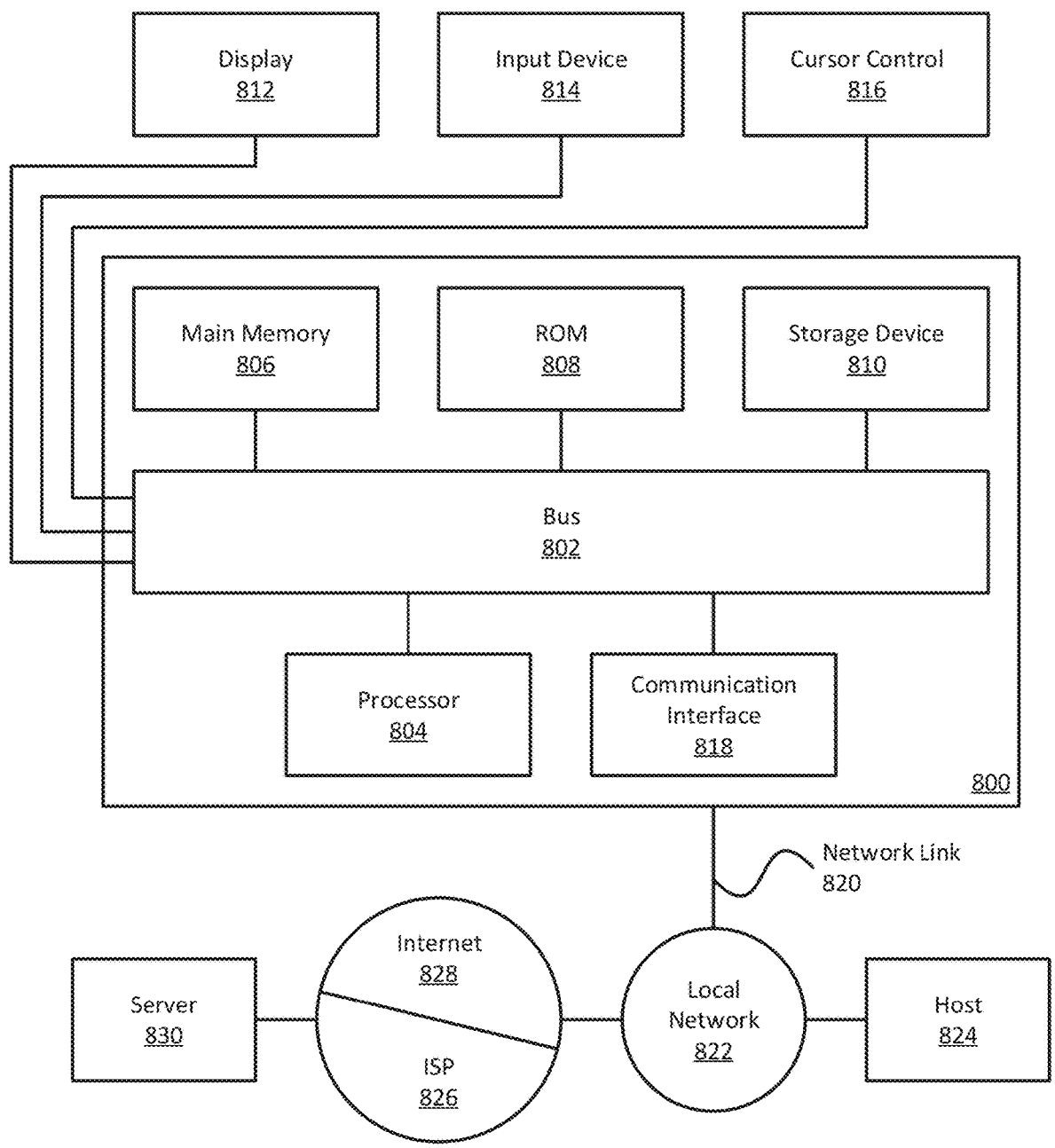
FIG. 8 is a block diagram of an example of a computer system according to an embodiment.

For example, FIG. 8 is a block diagram of an example of a computer system 800 according to an embodiment. Computer system 800 includes a bus 802 or other communication mechanism for communicating information, and a hardware processor 804 coupled with the bus 802 for processing information. Hardware processor 804 may be a general-purpose microprocessor.

Computer system 800 also includes a main memory 806, such as a random access memory (RAM) or other dynamic storage device, coupled to bus 802 for storing information and instructions to be executed by processor 804. Main memory 806 also may be used for storing temporary variables or other intermediate information during execution of instructions to be executed by processor 804. Such instructions, when stored in one or more non-transitory storage media accessible to processor 804, render computer system 800 into a special-purpose machine that is customized to perform the operations specified in the instructions.

Computer system 800 further includes a read only memory (ROM) 808 or other static storage device coupled to bus 802 for storing static information and instructions for processor 804. A storage device 810, such as a magnetic disk or optical disk, is provided and coupled to bus 802 for storing information and instructions.

Computer system 800 may be coupled via bus 802 to a display 812, such as a liquid crystal display (LCD), plasma display, electronic ink display, cathode ray tube (CRT) monitor, or any other kind of device for displaying information to a computer user. An input device 814, including alphanumeric and other keys, may be coupled to bus 802 for communicating information and command selections to processor 804. Alternatively or additionally, computer system 800 may receive user input via a cursor control 816, such as a mouse, a trackball, a trackpad, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane. Alternatively or additionally, computer system 8 may include a touchscreen. Display 812 may be configured to receive user input via one or more pressure-sensitive sensors, multi-touch sensors, and/or gesture sensors. Alternatively or additionally, computer system 800 may receive user input via a microphone, video camera, and/or some other kind of user input device (not shown).

Computer system 800 may implement the techniques described herein using customized hard-wired logic, one or more ASICs or FPGAs, firmware, and/or program logic which in combination with other components of computer system 800 causes or programs computer system 800 to be a special-purpose machine. According to one embodiment, the techniques herein are performed by computer system 800 in response to processor 804 executing one or more sequences of one or more instructions contained in main memory 806. Such instructions may be read into main memory 806 from another storage medium, such as storage device 810. Execution of the sequences of instructions contained in main memory 806 causes processor 804 to perform the process steps described herein. Alternatively or additionally, hard-wired circuitry may be used in place of or in combination with software instructions.

The term "storage media" as used herein refers to one or more non-transitory media storing data and/or instructions that cause a machine to operate in a specific fashion. Such storage media may comprise non-volatile media and/or volatile media. Non-volatile media includes, for example, optical or magnetic disks, such as storage device 810. Volatile media includes dynamic memory, such as main memory 806. Common forms of storage media include, for example, a floppy disk, a flexible disk, hard disk, solid state drive, magnetic tape or other magnetic data storage medium, a CD-ROM or any other optical data storage medium, any physical medium with patterns of holes, a RAM, a programmable read-only memory (PROM), an erasable PROM (EPROM), a FLASH-EPROM, non-volatile random-access memory (NVRAM), any other memory chip or cartridge, content-addressable memory (CAM), and ternary content-addressable memory (TCAM).

A storage medium is distinct from but may be used in conjunction with a transmission medium. Transmission media participate in transferring information between storage media. Examples of transmission media include coaxial cables, copper wire, and fiber optics, including the wires that comprise bus 802. Transmission media may also take the form of acoustic or light waves, such as those generated during radio-wave and infra-red data communications.

Various forms of media may be involved in carrying one or more sequences of one or more instructions to processor 804 for execution. For example, the instructions may initially be carried on a magnetic disk or solid state drive of a remote computer. The remote computer may load the instructions into its dynamic memory and send the instructions over a network, via a network interface controller (NIC), such as an Ethernet controller or Wi-Fi controller. A NIC local to computer system 800 may receive the data from the network and place the data on bus 802. Bus 802 carries the data to main memory 806, from which processor 804 retrieves and executes the instructions. The instructions received by main memory 806 may optionally be stored on storage device 810 either before or after execution by processor 804.

Computer system 800 also includes a communication interface 818 coupled to bus 802. Communication interface 818 provides a two-way data communication coupling to a network link 820 that is connected to a local network 822. For example, communication interface 818 may be an integrated services digital network (ISDN) card, cable modem, satellite modem, or a modem to provide a data communication connection to a corresponding type of telephone line. As another example, communication interface 818 may be a local area network (LAN) card to provide a data communication connection to a compatible LAN. Wireless links may also be implemented. In any such implementation, communication interface 818 sends and receives electrical, electromagnetic or optical signals that carry digital data streams representing various types of information.

Network link 820 typically provides data communication through one or more networks to other data devices. For example, network link 820 may provide a connection through local network 822 to a host computer 824 or to data equipment operated by an Internet Service Provider (ISP) 826. ISP 826 in turn provides data communication services through the world wide packet data communication network now commonly referred to as the "Internet" 828. Local network 822 and Internet 828 both use electrical, electromagnetic or optical signals that carry digital data streams. The signals through the various networks and the signals on network link 820 and through communication interface 818, which carry the digital data to and from computer system 800, are example forms of transmission media.

Computer system 800 can send messages and receive data, including program code, through the network(s), network link 820 and communication interface 818. In the Internet example, a server 830 might transmit a requested code for an application program through Internet 828, ISP 826, local network 822, and communication interface 818.

The received code may be executed by processor 804 as it is received, and/or stored in storage device 810, or other non-volatile storage for later execution.

In an embodiment, a computer network provides connectivity among a set of nodes running software that utilizes techniques as described herein. The nodes may be local to and/or remote from each other. The nodes are connected by a set of links. Examples of links include a coaxial cable, an unshielded twisted cable, a copper cable, an optical fiber, and a virtual link.

A set of nodes implements the computer network. Examples of such nodes include a switch, a router, a firewall, and a network address translator (NAT). Another set of nodes uses the computer network. Such nodes (also referred to as "hosts") may execute a client process and/or a server process. A client process makes a request for a computing service (for example, a request to execute a particular application and/or retrieve a particular set of data). A server process responds by executing the requested service and/or returning corresponding data.

A computer network may be a physical network, including physical nodes connected by physical links. A physical node is any digital device. A physical node may be a function-specific hardware device. Examples of function-specific hardware devices include a hardware switch, a hardware router, a hardware firewall, and a hardware NAT. Alternatively or additionally, a physical node may be any physical resource that provides compute power to perform a task, such as one that is configured to execute various virtual machines and/or applications performing respective functions. A physical link is a physical medium connecting two or more physical nodes. Examples of links include a coaxial cable, an unshielded twisted cable, a copper cable, and an optical fiber.

A computer network may be an overlay network. An overlay network is a logical network implemented on top of another network (for example, a physical network). Each node in an overlay network corresponds to a respective node in the underlying network. Accordingly, each node in an overlay network is associated with both an overlay address (to address the overlay node) and an underlay address (to address the underlay node that implements the overlay node). An overlay node may be a digital device and/or a software process (for example, a virtual machine, an application instance, or a thread). A link that connects overlay nodes may be implemented as a tunnel through the underlying network. The overlay nodes at either end of the tunnel may treat the underlying multi-hop path between them as a single logical link. Tunneling is performed through encapsulation and decapsulation.

In an embodiment, a client may be local to and/or remote from a computer network. The client may access the computer network over other computer networks, such as a private network or the Internet. The client may communicate requests to the computer network using a communications protocol, such as Hypertext Transfer Protocol (HTTP). The requests are communicated through an interface, such as a client interface (such as a web browser), a program interface, or an application programming interface (API).

In an embodiment, a computer network provides connectivity between clients and network resources. Network resources include hardware and/or software configured to execute server processes. Examples of network resources include a processor, a data storage, a virtual machine, a container, and/or a software application. Network resources may be shared amongst multiple clients. Clients request computing services from a computer network independently of each other. Network resources are dynamically assigned to the requests and/or clients on an on-demand basis. Network resources assigned to each request and/or client may be scaled up or down based on, for example, (a) the computing services requested by a particular client, (b) the aggregated computing services requested by a particular tenant, and/or (c) the aggregated computing services requested of the computer network. Such a computer network may be referred to as a "cloud network."

In an embodiment, a service provider provides a cloud network to one or more end users. Various service models may be implemented by the cloud network, including but not limited to Software-as-a-Service (SaaS), Platform-as-a-Service (PaaS), and Infrastructure-as-a-Service (IaaS). In SaaS, a service provider provides end users the capability to use the service provider's applications, which are executing on the network resources. In PaaS, the service provider provides end users the capability to deploy custom applications onto the network resources. The custom applications may be created using programming languages, libraries, services, and tools supported by the service provider. In IaaS, the service provider provides end users the capability to provision processing, storage, networks, and other fundamental computing resources provided by the network resources. Any applications, including an operating system, may be deployed on the network resources.

In an embodiment, various deployment models may be implemented by a computer network, including but not limited to a private cloud, a public cloud, and a hybrid cloud. In a private cloud, network resources are provisioned for exclusive use by a particular group of one or more entities (the term "entity" as used herein refers to a corporation, organization, person, or other entity). The network resources may be local to and/or remote from the premises of the particular group of entities. In a public cloud, cloud resources are provisioned for multiple entities that are independent from each other (also referred to as "tenants" or "customers"). In a hybrid cloud, a computer network includes a private cloud and a public cloud. An interface between the private cloud and the public cloud allows for data and application portability. Data stored at the private cloud and data stored at the public cloud may be exchanged through the interface. Applications implemented at the private cloud and applications implemented at the public cloud may have dependencies on each other. A call from an application at the private cloud to an application at the public cloud (and vice versa) may be executed through the interface.

In an embodiment, a system supports multiple tenants. A tenant is a corporation, organization, enterprise, business unit, employee, or other entity that accesses a shared computing resource (for example, a computing resource shared in a public cloud). One tenant (through operation, tenant-specific practices, employees, and/or identification to the external world) may be separate from another tenant. The computer network and the network resources thereof are accessed by clients corresponding to different tenants. Such a computer network may be referred to as a "multi-tenant computer network." Several tenants may use a same particular network resource at different times and/or at the same time. The network resources may be local to and/or remote from the premises of the tenants. Different tenants may demand different network requirements for the computer network. Examples of network requirements include processing speed, amount of data storage, security requirements, performance requirements, throughput requirements, latency requirements, resiliency requirements, Quality of Service (QoS) requirements, tenant isolation, and/or consistency. The same computer network may need to implement different network requirements demanded by different tenants.

In an embodiment, in a multi-tenant computer network, tenant isolation is implemented to ensure that the applications and/or data of different tenants are not shared with each other. Various tenant isolation approaches may be used. In an embodiment, each tenant is associated with a tenant ID. Applications implemented by the computer network are tagged with tenant ID's. Additionally or alternatively, data structures and/or datasets, stored by the computer network, are tagged with tenant ID's. A tenant is permitted access to a particular application, data structure, and/or dataset only if the tenant and the particular application, data structure, and/or dataset are associated with a same tenant ID. As an example, each database implemented by a multi-tenant computer network may be tagged with a tenant ID. Only a tenant associated with the corresponding tenant ID may access data of a particular database. As another example, each entry in a database implemented by a multi-tenant computer network may be tagged with a tenant ID. Only a tenant associated with the corresponding tenant ID may access data of a particular entry. However, the database may be shared by multiple tenants. A subscription list may indicate which tenants have authorization to access which applications. For each application, a list of tenant ID's of tenants authorized to access the application is stored. A tenant is permitted access to a particular application only if the tenant ID of the tenant is included in the subscription list corresponding to the particular application.

In an embodiment, network resources (such as digital devices, virtual machines, application instances, and threads) corresponding to different tenants are isolated to tenant-specific overlay networks maintained by the multi-tenant computer network. As an example, packets from any source device in a tenant overlay network may only be transmitted to other devices within the same tenant overlay network. Encapsulation tunnels may be used to prohibit any transmissions from a source device on a tenant overlay network to devices in other tenant overlay networks. Specifically, the packets, received from the source device, are encapsulated within an outer packet. The outer packet is transmitted from a first encapsulation tunnel endpoint (in communication with the source device in the tenant overlay network) to a second encapsulation tunnel endpoint (in communication with the destination device in the tenant overlay network). The second encapsulation tunnel endpoint decapsulates the outer packet to obtain the original packet transmitted by the source device. The original packet is transmitted from the second encapsulation tunnel endpoint to the destination device in the same particular overlay network.

What is claimed is:

1. One or more non-transitory computer-readable media storing instructions that, when executed by one or more processors, predict one or more intradialytic hypotensive (IDH) events by:
   using a machine learning model to determine the probability of a future IDH event occurring based on training of the machine learning model; and
   using the machine learning model to make a prediction that the future IDH event will occur in a time period beginning at least a second amount of time after making the prediction based on the training of the machine learning model, the machine learning model being trained by
      obtaining historical hemodialysis treatment data preceding one or more intradialytic hypotension (IDH) events,
      segmenting a first portion of the historical hemodialysis treatment data into a first set, the first portion of the historical hemodialysis treatment data being data obtained before a first amount of time preceding the IDH events,
      segmenting a second portion of the historical hemodialysis treatment data into a second set, the second portion of the historical hemodialysis treatment data being data obtained after the first amount of time and before the second amount of time preceding the IDH events,
      segmenting a third portion of the historical hemodialysis treatment data into a third set, the third portion of the historical hemodialysis treatment data being data obtained after the second amount of time and before the IDH events; and
      in a first stage, training the machine learning model to predict the occurrence of IDH events based on the second set, the machine learning model treating the second set as containing data indicative of a future IDH event occurring after at least the second amount of time after making a prediction that the future IDH event will occur, and
      in a second stage, training the machine learning model to predict the occurrence of IDH events based on the first set, the machine learning model treating the first set as containing data not indicative of the future IDH event; and
      wherein, the training of the machine learning model in either the first or the second stage does not utilize the third set of the historical hemodialysis treatment data nor any data occurring after the IDH events;
   obtaining real-time hemodialysis data associated with a hemodialysis patient; and
   applying the real-time hemodialysis data to the machine learning model, to predict whether the probability of the future IDH event occurring within the second amount of time is greater than a threshold probability for the hemodialysis patient.

2. The one or more non-transitory computer-readable media of claim 1, wherein the first amount of time is an amount of time of at least seventy-five minutes and the second amount of time is an amount of time of at least fifteen minutes.

3. The one or more non-transitory computer-readable media of claim 1, further storing instructions that, when executed by one or more processors, cause: responsive to making the prediction that the future IDH event will occur at least the second amount of time after making the prediction, adjusting without human intervention a treatment of the hemodialysis patient to prevent the future IDH event.

4. The one or more non-transitory computer-readable media of claim 3, wherein adjusting without human intervention the treatment of the hemodialysis patient comprises one or more of reducing an ultrafiltration rate, decreasing a dailysate temperature, or mechanically repositioning the hemodialysis patient.

5. The one or more non-transitory computer-readable media of claim 1, wherein the machine learning model makes the prediction each time the hemodialysis patient's intradialytic systolic blood pressure is measured.

6. The one or more non-transitory computer-readable media of claim 1, wherein the second amount of time before the IDH events is set to an amount of time to ensure that predictions of IDH events allow for enough time for clinical intervention.

7. A system comprising:
   at least one device including a hardware processor;
   the system being configured to perform operations comprising:
   using a machine learning model to determine the probability of a future intradialytic hypotensive (IDH) event occurring based on training of the machine learning model; and
   using the machine learning model to make a prediction that the future IDH event will occur in a time period beginning at least a second amount of time after making the prediction based on the training of the machine learning model, the machine learning model being trained by
      obtaining historical hemodialysis treatment data preceding one or more intradialytic hypotension (IDH) events,
      segmenting a first portion of the historical hemodialysis treatment data into a first set, the first portion of the historical hemodialysis treatment data being data obtained before a first amount of time preceding the IDH events,
      segmenting a second portion of the historical hemodialysis treatment data into a second set, the second portion of the historical hemodialysis treatment data being data obtained after the first amount of time and before the second amount of time preceding the IDH events,
      segmenting a third portion of the historical hemodialysis treatment data into a third set, the third portion of the historical hemodialysis treatment data being data obtained after the second amount of time and before the IDH events; and
      in a first stage, training the machine learning model to predict the occurrence of IDH events based on the second set, the machine learning model treating the second set as containing data indicative of a future IDH event occurring after at least the second amount of time after making a prediction that the future IDH event will occur, and in a second stage, training the machine learning model to predict the occurrence of IDH events based on the first set, the machine learning model treating the first set as containing data not indicative of the future IDH event; and wherein, the training of the machine learning model in either the first or the second stage does not utilize the third set of the historical hemodialysis treatment data nor any data occurring after the IDH events;

obtaining real-time hemodialysis data associated with a hemodialysis patient; and applying the real-time hemodialysis data to the machine learning model, to predict whether the probability of the future IDH event occurring within the second amount of time is greater than a threshold probability for the hemodialysis patient.

8. The system of claim 7, wherein the first amount of time is an amount of time of at least seventy-five minutes and the second amount of time is an amount of time of at least fifteen minutes the plurality of sets of machine learning training data comprises.

9. The system of claim 7, the operations further comprising:

responsive to making the prediction that the future IDH event will occur at least the second amount of time after making the prediction, adjusting without human intervention a treatment of the hemodialysis patient to prevent the future IDH event.

10. The system of claim 9, wherein adjusting without human intervention the treatment of the hemodialysis patient comprises one or more of reducing an ultrafiltration rate, decreasing a dialysate temperature, or mechanically repositioning the hemodialysis patient.

11. A method comprising:

using a machine learning model to determine the probability of a future intradialytic hypotensive (IDH) event occurring based on training of the machine learning model; and using the machine learning model to make a prediction that the future IDH event will occur in a time period beginning at least a second amount of time after making the prediction based on the training of the machine learning model, the machine learning model being trained by obtaining historical hemodialysis treatment data preceding one or more intradialytic hypotension (IDH) events, segmenting a first portion of the historical hemodialysis treatment data into a first set, the first portion of the historical hemodialysis treatment data being data obtained before a first amount of time preceding the IDH events, segmenting a second portion of the historical hemodialysis treatment data into a second set, the second portion of the historical hemodialysis treatment data being data obtained after the first amount of time and before the second amount of time preceding the IDH events, segmenting a third portion of the historical hemodialysis treatment data into a third set, the third portion of the historical hemodialysis treatment data being data obtained after the second amount of time and before the IDH events; and in a first stage, training the machine learning model to predict the occurrence of IDH events based on the second set, the machine learning model treating the second set as containing data indicative of a future IDH event occurring after at least the second amount of time after making a prediction that the future IDH event will occur, and in a second stage, training the machine learning model to predict the occurrence of IDH events based on the first set, the machine learning model treating the first set as containing data not indicative of the future IDH event; and wherein, the training of the machine learning model in either the first or the second stage does not utilize the third set of the historical hemodialysis treatment data nor any data occurring after the IDH events;

obtaining real-time hemodialysis data associated with a hemodialysis patient; and applying the real-time hemodialysis data to the machine learning model, to predict whether the probability of the future IDH event occurring within the second amount of time is greater than a threshold probability for the hemodialysis patient.

12. The method of claim 11, wherein the first amount of time is an amount of time of at least seventy-five minutes and the second amount of time is an amount of time of at least fifteen minutes the plurality of sets of machine learning training data comprises.

13. The method of claim 11, further comprising: responsive to making the prediction that the future IDH event will occur at least the second amount of time after making the prediction, adjusting without human intervention a treatment of the hemodialysis patient to prevent the future IDH event.

14. The method of claim 13, wherein adjusting without human intervention the treatment of the hemodialysis patient comprises one or more of reducing an ultrafiltration rate, decreasing a dialysate temperature, or mechanically repositioning the hemodialysis patient.

15. The method of claim 11 wherein the machine learning model makes the prediction each time the hemodialysis patient's intradialytic systolic blood pressure is measured.

* * * * *

UNITED STATES PATENT AND TRADEMARK OFFICE
CERTIFICATE OF CORRECTION

| | | |
|---|---|---|
| PATENT NO. | : 12,040,092 B2 | |
| APPLICATION NO. | : 16/897430 | |
| DATED | : July 16, 2024 | |
| INVENTOR(S) | : Peter Kotanko et al. | |

It is certified that error appears in the above-identified patent and that said Letters Patent is hereby corrected as shown below:

In the Claims

Column 20, Line 22, Claim number 4, delete "dailysate" and insert -- dialysate --.

Signed and Sealed this
Twentieth Day of August, 2024

Katherine Kelly Vidal
*Director of the United States Patent and Trademark Office*